(12) United States Patent
Schostek et al.

(10) Patent No.: US 9,215,968 B2
(45) Date of Patent: Dec. 22, 2015

(54) MAGNETIC END EFFECTOR AND DEVICE FOR GUIDING AND POSITIONING THE SAME

(71) Applicant: Ovesco Endoscopy AG, Tuebingen (DE)

(72) Inventors: Sebastian Schostek, Tuebingen (DE); Thomas Gottwald, Kochel am See (DE); Marc O. Schurr, Tuebingen (DE)

(73) Assignee: Ovesco Endoscopy AG, Tuebingen (DE)

( * ) Notice: Subject to any disclaimer, the term of this patent is extended or adjusted under 35 U.S.C. 154(b) by 318 days.

(21) Appl. No.: 13/660,097

(22) Filed: Oct. 25, 2012

(65) Prior Publication Data
US 2013/0110128 A1    May 2, 2013

(30) Foreign Application Priority Data
Oct. 28, 2011   (DE) .......................... 10 2011 054 910

(51) Int. Cl.
*A61B 1/04*    (2006.01)
*A61B 1/045*   (2006.01)
*A61B 1/00*    (2006.01)
*B25J 19/06*   (2006.01)
*B25J 19/00*   (2006.01)

(52) U.S. Cl.
CPC ......... *A61B 1/00158* (2013.01); *B25J 19/0008* (2013.01); *B25J 19/06* (2013.01); *A61B 1/041* (2013.01)

(58) Field of Classification Search
CPC .... A61B 1/00133; A61B 1/041; A61B 1/045; A61B 1/00147; A61B 1/00149; A61B 1/00158; A61B 1/0016; A61B 5/6861; A61B 5/06; A61B 5/062; A61B 5/07; A61B 2562/165
USPC ........................................................ 128/899
See application file for complete search history.

(56) References Cited

U.S. PATENT DOCUMENTS

| 4,269,066 A | 5/1981 | Fischer |
| 5,332,181 A | 7/1994 | Schweizer |

(Continued)

FOREIGN PATENT DOCUMENTS

| DE | 3029449 A1 | 3/1981 |
| DE | 10335644 | 12/2005 |

(Continued)

OTHER PUBLICATIONS

German Application No. 10 2011 054 910.2 Official Action mailed Mar. 5, 2013 with English translation.

(Continued)

*Primary Examiner* — Charles A Marmor, II
*Assistant Examiner* — Thaddeus Cox
(74) *Attorney, Agent, or Firm* — RatnerPrestia

(57) ABSTRACT

A magnetic guiding device (robotics) for an intracorporeal object includes a motor-driven positioning device having a maximum of three degrees of freedom to be activated for translational motion of a connecting interface of the positioning device to which a magnetic end effector is connected or connectable, the latter including a maximum of two degrees of freedom to be activated for rotational motion of a magnetic field generator. At least one of the two degrees of freedom of the magnetic end effector is encased in an effector housing.

15 Claims, 12 Drawing Sheets

(56) References Cited

U.S. PATENT DOCUMENTS

Figure 1:
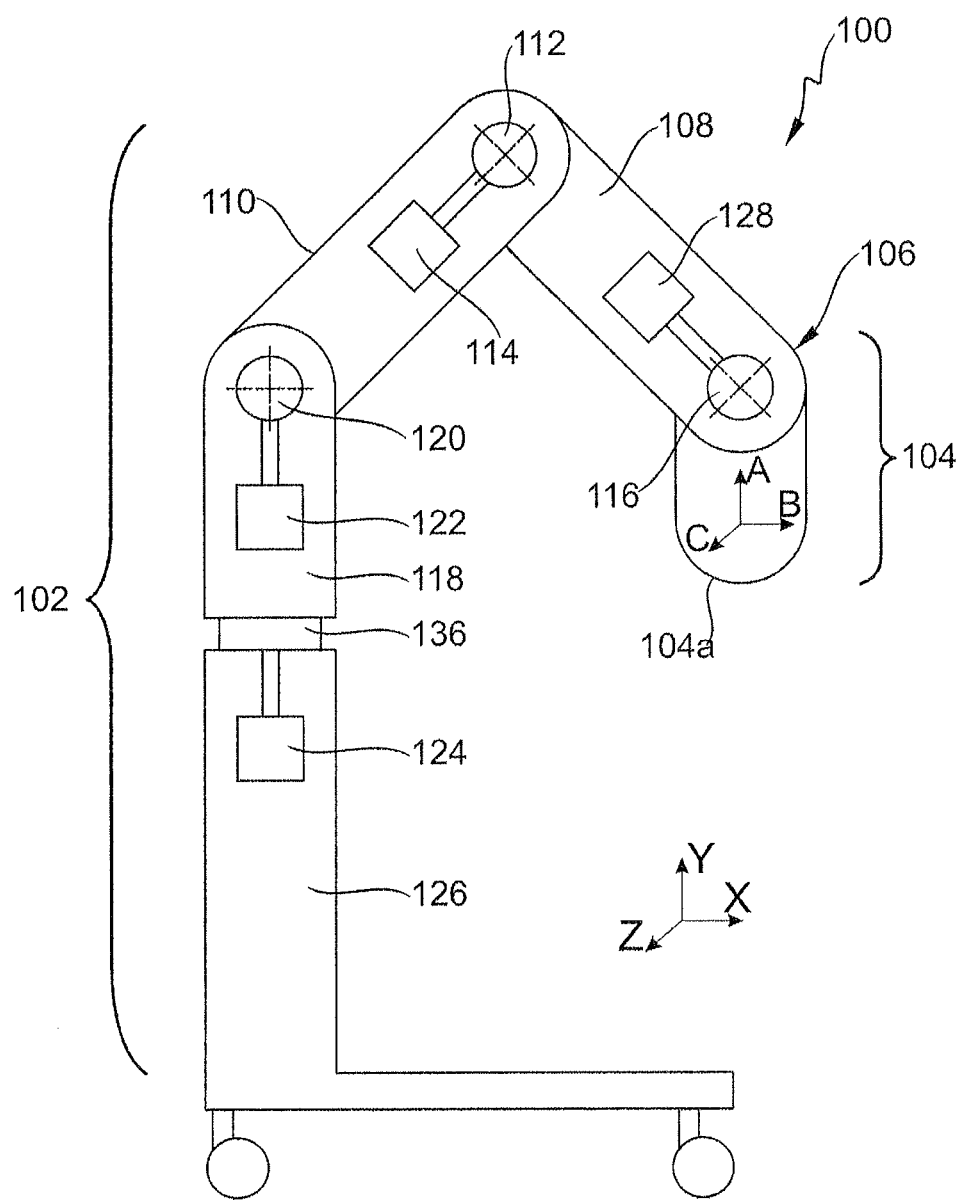

| | | | |
|---|---|---|---|
| 6,626,834 B2* | 9/2003 | Dunne et al. | 600/444 |
| 7,190,513 B2 | 3/2007 | Obrebski | |
| 2005/0154431 A1* | 7/2005 | Quistgaard et al. | 607/96 |
| 2007/0221233 A1 | 9/2007 | Kawano | |
| 2008/0300458 A1* | 12/2008 | Kim et al. | 600/118 |
| 2009/0003975 A1* | 1/2009 | Kuduvalli et al. | 414/146 |
| 2011/0072918 A1* | 3/2011 | Reekers | 74/55 |

FOREIGN PATENT DOCUMENTS

| | | |
|---|---|---|
| EP | 0554711 | 8/1993 |
| EP | 2347699 A1 | 7/2011 |
| KR | 100735863 | 6/2007 |
| WO | 03099152 | 12/2003 |
| WO | 2009107892 | 9/2009 |

OTHER PUBLICATIONS

German Application Serial No. 102011054910.2, German Search Report dated Jun. 27, 2012, 6 pgs. (partial English translation).

Ciuti et al., "Robotic magnetic steering and locomotion of capsule endoscope for diagnostic and surgical endoluminal procedures," Robotica, vol. 28, Jan. 1, 2010, pp. 199-207, published Oct. 26, 2009.

European Search Report mailed Feb. 26, 2015 for European Application No. 12190320.7, with partial English translation.

Fountain et al., "Wireless control of magnetic helical microrobots using a rotating-permanent-magnet manipulator," 2010 IEEE International Conference on Robotics and Automation, May 3-8, 2010, Anchorage, Alaska, pp. 576-581.

* cited by examiner

Fig. 6
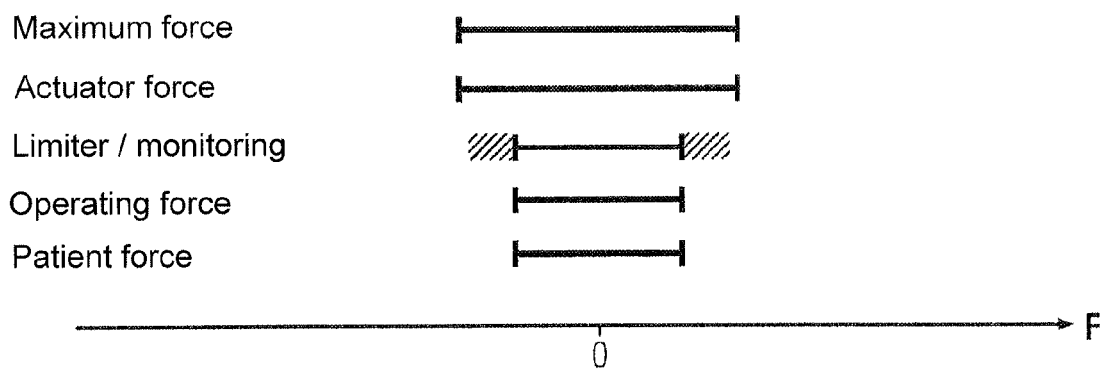
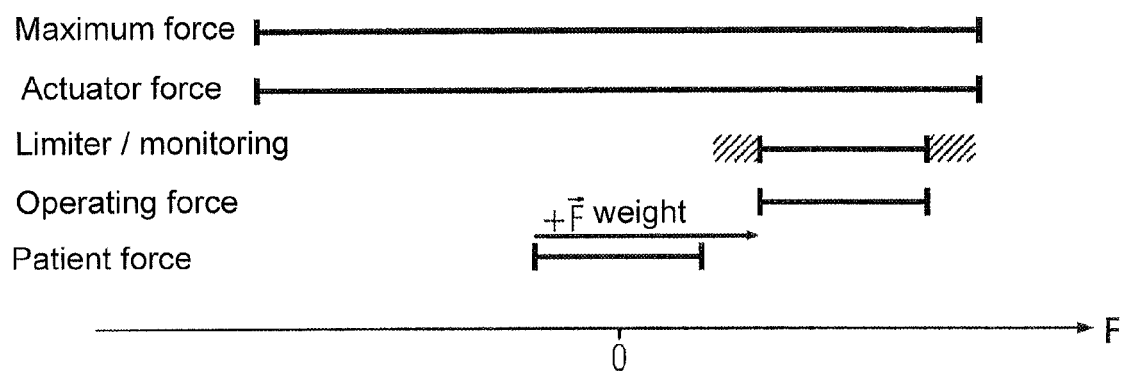
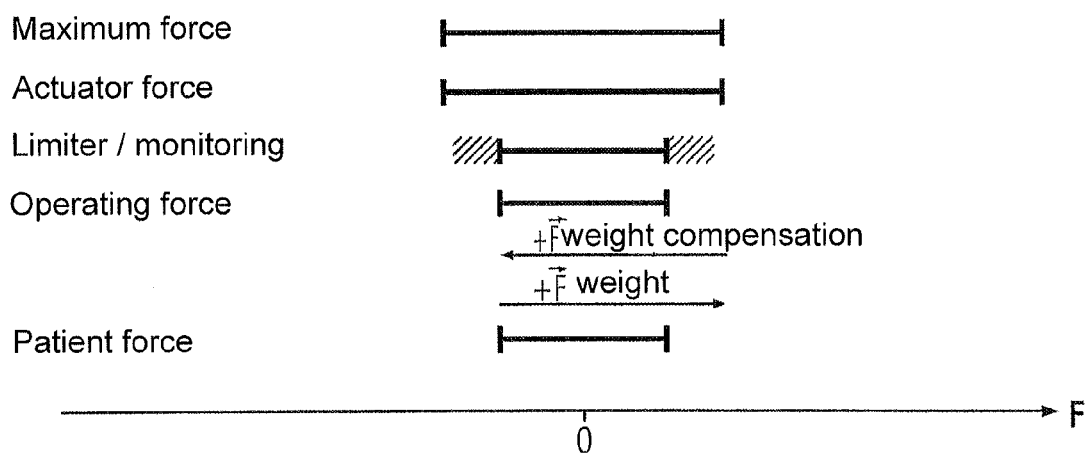

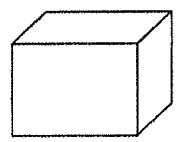 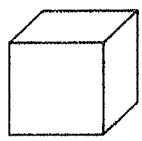 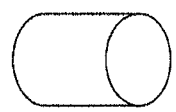
Fig. 10a　　　Fig. 10b　　　Fig. 10c
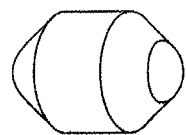 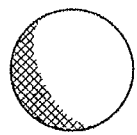
Fig. 10d　　　Fig. 10e
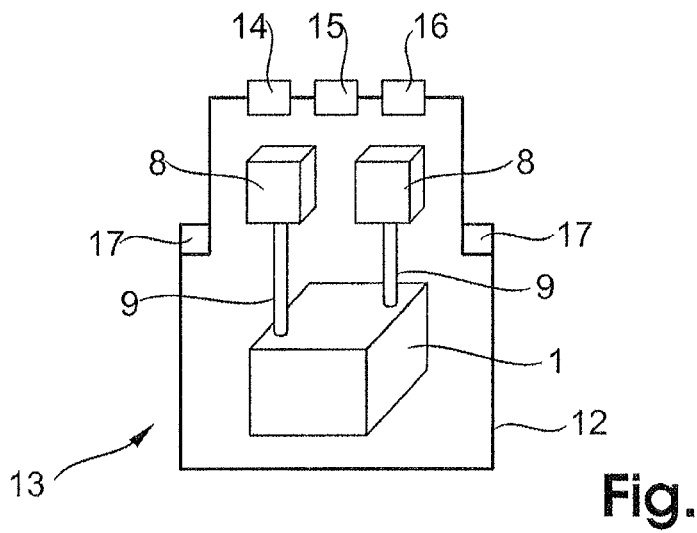
Fig. 11a
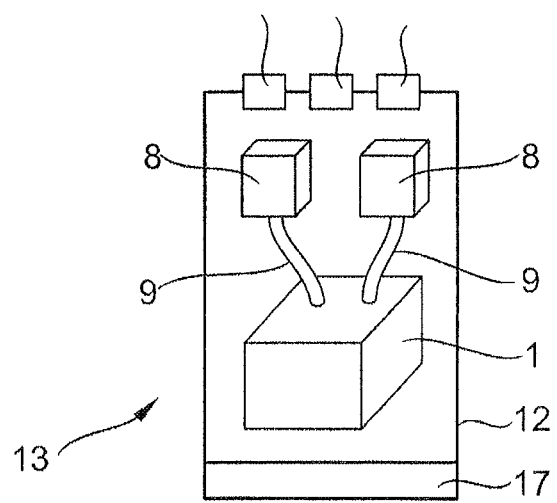
Fig. 11b

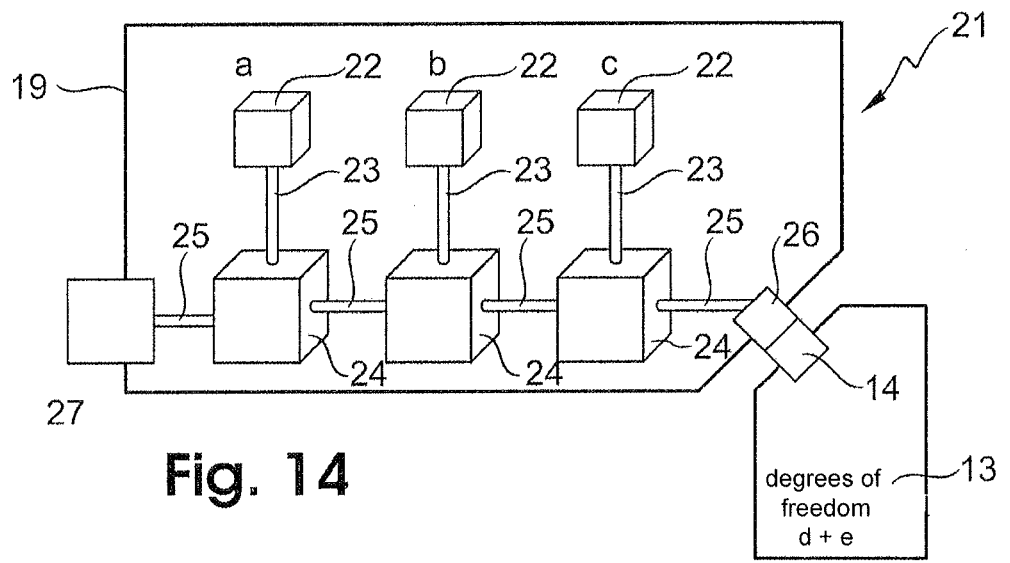
Fig. 14
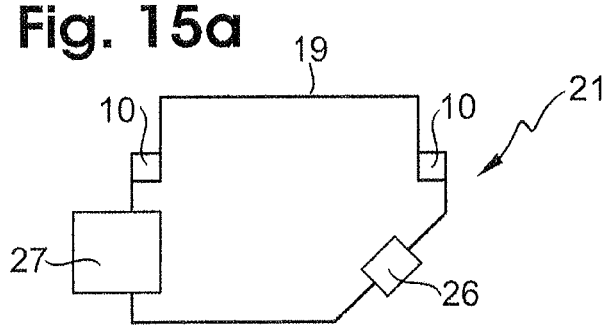
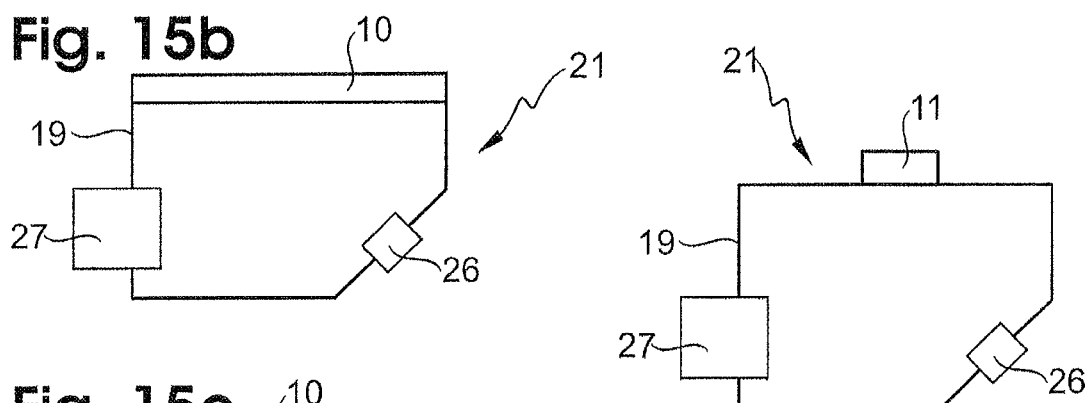
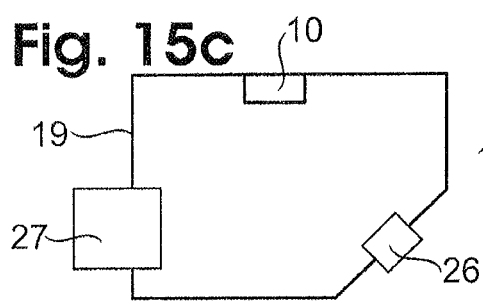
Fig. 16

MAGNETIC END EFFECTOR AND DEVICE FOR GUIDING AND POSITIONING THE SAME

CROSS-REFERENCE TO RELATED APPLICATIONS

This application claims priority to German Patent Application No. DE 10 2011 054 910.2, filed Oct. 28, 2011, the contents of which are incorporated by reference herein in their entirety.

FIELD OF THE INVENTION

The present invention in general relates to a medical robot system for magnetic guiding of a probe and especially to a magnetic guiding device for an intracorporeal object, preferably an endoscopic capsule or a catheter. The guiding device according to aspects of the invention will be described hereinafter by the example of application in medicine. However, the invention can be conferred, in its full content, upon other technical systems. Such technical system can be, for instance, a tubing system in which the object to be controlled is provided.

BACKGROUND OF THE INVENTION

In medicine systems (robot systems) for (manual or preprogrammed) control of intracorporeal objects by means of extracorporeally generated magnetic fields are known. Intracorporeal objects, for instance endoscopic capsules, probes or catheters, to this effect have an element adapted to be influenced by magnetic fields, e.g. a permanent magnet which is mounted in the object. The orientation and/or positioning of the intracorporeal objects can be controlled by extracorporeally generated magnetic fields. For providing extracorporeal magnetic fields likewise systems for generating electromagnetic gradient fields, for instance in the form of magnetic resonance imaging scanners, electromagnetic spot fields, e.g. by a solenoid in compact design, as well as systems including a permanent magnet are known.

Systems for generating electromagnetic gradient fields, for instance according to the design of magnetic resonance imaging scanners, have the drawback that, compared to other electrical equipment common in medical practices or in hospitals, these apparatuses have a very high power requirement and, due to their design, are very large and heavy compared to technical apparatuses otherwise common in medical practices or hospitals. Advantages of the systems according to the design of magnetic resonance imaging scanners are, however, that the gradient field can be set to be finely adjusted and reproducible at the location of the intracorporeal objects for controlling the same and that a risk for the patient by movable components can be largely excluded, because the movable parts are provided inside a rigid shell statically surrounding the patient.

Hereinafter, by the term "magnetic field generator of compact design" those apparatuses are to be understood which generate a magnetic field extending in space around the apparatus so that the apparatus is provided in the center of the generated magnetic field. In particular, the range of use of those magnetic fields generated by magnetic field generators of compact design extends in the spatial environment of said magnetic field generators. In contrast to that are generators of a gradient field, for instance according to the design of a magnetic resonance imaging scanner whose range of use extends to the interior of an annular apparatus into which a patient has to be moved, i.e. the useful magnetic field is not intended to surround the magnetic field generator but to extend in a direction (radially inwards of the annular apparatus) away from the same. Magnetic field generators of compact design can consist, for example, of one or more solenoids or one or more permanent magnets or of combinations of the two.

The term "force" as generally used hereinafter can describe a mechanical force or a torque.

The use of magnetic field generators of compact design according to the above definition has the advantage that the apparatuses have a similar power requirement compared to other electrical equipment common in medical practices or hospitals and, due to their design, have a similar size and weight compared to technical apparatuses otherwise common in medical practices or hospitals. That is, they are basically suited also for mobile use in a practice or hospital with normal effort. However, a drawback of the use of magnetic field generators of compact design for the control of an intracorporeal object resides in the fact that for adjusting the magnetic field at the location of the intracorporeal object the position and orientation of the magnetic field generator of compact design (e.g. permanent magnet or solenoid) in space is required, i.e. the magnetic field generator of compact design must be moved in space relative to a patient. According to current prior art, the orientation of the magnetic field generator of compact design in space is achieved either manually or by actuated (motor-driven) robotic devices, i.e. magnetic guiding devices as they are called. Another drawback of magnetic field generators of compact design is that the intensity of the magnetic field in the range of use is strongly reduced with an increasing distance from the magnetic field generator. For this reason it is advantageous and possibly also necessary to position the magnetic field generators of compact design as closely as possible to the intracorporeal object to be controlled so that an impact of the magnetic field on the intracorporeal object sufficient for the control of the intracorporeal object is provided.

The manually guided orientation of the magnetic field generator of compact design has the advantage that the structure may exhibit minimum complexity. Embodiments include the movement of a hand-held permanent magnet as well as manually guided passive, i.e. not actuated assistance systems for compensating the weight of the magnetic field generator of compact design. It is a further advantage that the controlling person gets a permanent information feedback on the motion parameters and especially collisions with and action of force upon a patient's body by the manual orientation of the magnetic field generator of compact design by at least his/her haptic sense and that thus actions endangering the patient can be avoided when orientating the magnetic field generator of compact design. The manually guided orientation of the magnetic field generator of compact design in space has the drawback, however, that the controlling effect of orientating motions of the magnetic field generator of compact design on the orientation of the intracorporeal object are not intuitively predictable, because the controlling person has no direct visual connection to the intracorporeal object and thus obtains no information about the current position and orientation of the same. That is to say, no direct information about the current position and orientation of the intracorporeal object can be conveyed to the controlling person via the magnetic field generator, which would be analogous to a visual flight at night. It is clear that a guiding method based on the afore-described devices is feasible only with very much practice and presumably with insufficient results. This fact is described in detail in EP 2 347 699 A1, which is incorporated by reference in its entirety, for instance.

The robot-guided orientation of the magnetic field generator of compact design in space on the other hand has the advantage that by direct information feedback between the intracorporeal object and the robotic device controlling the magnetic field generator of compact design (robot arm) a control of the position and the orientation of the intracorporeal object intuitive and predictable to the controlling person can be obtained. The principle of such information feedback is disclosed in the afore-mentioned EP 2 347 699 A1 so that in this context the respective publication can be referred to for complete understanding of the present technical teaching.

A robot-guided orientation of the magnetic field generator of compact design in space has the drawback, however, that the apparatus for robot-guided orientation of the magnetic field generator of compact design basically can perform also those movements which might result in a collision with and without action of force on a patient's body and thus in actions endangering the patient or the controlling person upon his/her body. In other words, robots of conventional conception are easily capable of fatally injuring a person or damaging neighboring objects in the case of a wrong movement so that typically a safety area has to be closed off in the field of motion of the respective robot.

As explained already in the foregoing, it is of advantage to position the magnetic field generator of compact design as closely as possible to the intracorporeal object to be controlled so as to exert sufficient magnetic attraction on the object. It can even be of advantage to press the magnetic field generator of compact design with a defined force onto a patient's body so as to form an indentation of the body for example in the abdominal region which enables the magnetic field generator of compact design to be positioned even more closely to the intracorporeal object to be controlled. In such situation movements of the magnetic field generator can be directly (mechanically) transmitted to a patient's body both for positioning and orientation of the magnetic field generator of compact design and can result in impacts on the patient's body endangering the patient. It is also obvious that safety areas in the conventional meaning are not applicable in this case.

It is technically possible to establish so called virtual barriers so as to prevent collisions or excessive force actions on the patient's body. Virtual barriers are limits deposited in the software of the control system of the device for the robot-guided orientation of the magnetic field generator of compact design in the form of space coordinates or actuator positions that are not exceeded in the case of intended function of the device, i.e. there is basically the possibility of virtually establishing the afore-mentioned safety area by programming measures. However, it is a drawback of this technical measure that the individual anatomic facts of patients (stout, slim, male, female etc.) cannot be taken into account. Consequently, the best possible approximation of the magnetic field generator of compact design to the intracorporeal object to be controlled is no longer given in each case. A further drawback of virtual barriers consists in the fact that they are implemented on a software level and thus further measures have to be taken on a software level for detecting malfunctions. Malfunctions possibly cannot be detected or mastered early enough by a user who is not technically versed.

In contrast to a virtual barrier according to the afore-mentioned definition, also a patient's body to be examined can be separated by a physically existent rigid barrier such as a cage from the device for robot-guided orientation of the magnetic field generator of compact design so as to eliminate the risk of impacts on the patient's body endangering the patient (crash protection). Drawbacks of this technical measure are, however, that the rigid barrier itself requires some space which is no longer available to the device for robot-guided orientation of the magnetic field generator of compact design and said barrier cannot take the individual anatomic facts of patients into account, either, unless the rigid physical barrier includes adjusting options so as to at least approach the same to the patient's anatomy. Thus the action of force on the patient's body advantageous to the approach of the magnetic field generator of compact design is no longer possible, i.e. by this technical solution of disposing a physical barrier the best possible approach of the magnetic field generator of compact design to the intracorporeal object to be controlled is no longer given (in each case), either.

Especially when applying actuated (motor-driven) systems in medical practice or hospital, it is necessary to meet strict safety requirements on the basis of risk disclosures. Risks for patients by the robot-guided orientation of a magnetic field generator of compact design inter alia result from the movements of the device for positioning and/or orientation of the magnetic field generator of compact design that may entail collisions with or without action of force upon the patient's body and thus impacts on the patient's body endangering the patient.

To make things worse, on particular conditions predefined collisions with or without action of force upon the patient's body can even be advantageous, for example in order to move the magnetic field generator of compact design as closely as possible to the intracorporeal object to be controlled, as this has already been indicated before. In this case a sensory feedback of the action of force of the device for the robot-guided orientation of the magnetic field generator of compact design on the patient's body is of advantage/necessary so as to specifically produce and also restrict the action of force. In this way, the action of force upon the patient's body can be kept within a range that does not endanger the patient. However, the problem in this case is that sensors for detecting the situation of collision may fail or provide wrong measuring results, the latter malfunction possibly being not realized not at all or too late (for the patient).

What is moreover crucial to a risk disclosure of such device is the question which actuated (motor-generated) maximum force can be exerted on the patient in the case of malfunction. For instance, a malfunction of a sensor can lead to the fact that the device increases the action of force on the patient's body beyond the range which does not endanger the patient, viz. to a range which endangers the patient. For this, the actuators or motor drives such as electric motors, piezo drives, hydraulic or pneumatic control pistons, electromagnetic drives etc. used in the device are required to be able to/have to generate a greater force than provided in the intended function.

The robotic guide of a magnetic field generator of compact design requires orientation of the magnetic field generator of compact design with (a maximum of) five degrees of freedom of motion. Said five degrees of freedom are translational motions along the three spatial axes disposed at right angles with each other as well as the rotation about those spatial axes that are normal to each other and preferably normal to the axis of polarization of the magnetic field generated by the magnetic field generator of compact design and hereinafter are referred to as pitching and yawing motion. The axis of polarization is co-linear with respect to the connecting line between the north and south magnetic poles of the magnetic field generator of compact design. Since rotation of the magnetic field generator of compact design about said polarization axis of the magnetic field (currently defined as "rolling motion") does not result in a change of the magnetic field in space, this orientation of the magnetic field generator of compact design by the device for robot guiding thereof is not expedient or is technically meaningless and thus superfluous.

Devices for robot-guided orientation of a magnetic field generator of compact design preferably are robot arms or extensions. Commercially available robot arms known today are largely used in automation engineering and are optimized to high travel rates, high precision as well as variability in tracking and load bearing.

In the robot-guided orientation of a magnetic field generator of compact design for the control of intracorporeal objects, on the other hand, the usual travel velocities are definitely lower than the travel velocities common in automation engineering. Whereas in automation engineering travel velocities are within the magnitude of up to 10 meters per second, in the use of a device for robot-guided orientation of a magnetic field generator of compact design according to aspects of the present invention definitely lower travel velocities are required, for example within the range of up to 0.1 meter per second. The drawback of commercially available robot arms known today for automation engineering resides in the fact that the actuating elements are designed for high velocities and therefore can release great forces. Moreover, robots of this species frequently have to carry and move heavy loads (including the dead weight of the robot arms) so that great driving forces and/or torques are required to move the robot arms. For this reason, in automation engineering those robot arms are used exclusively within rigid barriers as explained already in the foregoing. When used for a robot-guided orientation of a magnetic field generator of compact design, controlling errors or malfunctions therefore can lead to impacts on the patient's body endangering the patient.

However, in the robot-guided orientation of a magnetic field generator of compact design for the control of intracorporeal objects according to the aspects of present invention requirements to the precision and the variability of tracking and load bearing are definitely lower than usual today in automation engineering. For accurately orientating an intracorporeal object precision of the movement of the extracorporeal magnetic field generator of compact design within the range of millimeters up to one centimeter is completely sufficient, because the dislocation of the magnetic field generator of compact design within this range results in an only insignificant change of the magnetic field at the location of the intracorporeal object. Furthermore, in the robot-guided orientation of a magnetic field generator of compact design for the control of intracorporeal objects the requirements to variability of tracking are restricted due to the number of the degrees of freedom to be actuated which is limited to five as well as the limited operating range extending around the patient's body compared to the requirements common in automation engineering. Further, in automation engineering variable robots which are suited for different tasks and maneuvers and which can be adapted to different loads are frequently used. On the other hand, the magnetic field generator of compact design according to aspects of the present invention constitutes a constant load that is not varying. The device for robot-guided orientation of the magnetic field generator of compact design therefore always has the same load, whereas in automation engineering different and dynamically changing loads are usual.

In the robot-guided orientation of a magnetic field generator of compact design for the control of intracorporeal objects the requirements to precision, variability of tracking and load bearing as described in the foregoing are definitely lower compared to the requirements in automation engineering.

Using a robot from automation engineering as a device for robot-guided orientation of a magnetic field generator of compact design for the control of intracorporeal objects thus has the basic drawback that the design of the robot arm more than meets the requirements of the use as device for robot-guided orientation of a magnetic field generator of compact design according to aspects of the present invention for the control of intracorporeal objects such that this constitutes a risk for the patient and the operators. The specifications of the actuating elements of such robot which was designed for automation engineering moreover permit impacts on the patient's body endangering the patient.

On principle, experts strive for reducing over-dimensioned devices by so called "down-sizing" or reducing their power so that they are just adapted to fulfill the functions they are meant for. In the present case, however, the requirements to the robot and the magnetic guiding device are opposed, namely to the effect that, on the one hand, they must not be a risk for the patient and/or the operators and, on the other hand, they have to be sufficiently robust to withstand a permanent manual (even inappropriate) handling with all odds in a practice or hospital. Therefore, simple "down-sizing" according to known examples would not lead to a satisfactory result.

SUMMARY

In view of the foregoing problems, disclosed herein is a device for robot-guided orientation of a magnetic field generator of compact design, especially an extracorporeal guiding device of an intracorporeal magnetic object such as an endoscope capsule which is optimized with respect to the patient's safety but at the same time permits performing the required maneuvers without the restrictions known from the above-discussed technical solutions.

The foregoing problems are overcome by a (magnetic) extracorporeal guiding device (preferably in the form of articulated-arm/SCARA-type robotics, combined with telescopic robot arms, where appropriate) comprising a motor-driven positioning device having a maximum of three degrees of freedom to be activated namely for translational motion of a distal connecting interface of the positioning device in an extracorporeal space coordinate system to which an end effector of the extracorporeal guiding device is connected or connectable, the end effector having a maximum of two degrees of freedom to be activated namely for rotational motion of a magnetic field generator, preferably a permanent magnet of the end effector, wherein at least one of the two degrees of freedom of the end effector is encased in an effector housing.

The device for robot-guided orientation of a magnetic field generator of compact design is designed so that selectively the orientation of the individual degrees of freedom of the magnetic field generator of compact design in total or in a selected manner is separated, i.e. shielded from the patient's body and/or the action of force on the patient's body is restricted when operating the individual degrees of freedom preferably by the design of the respective drives for operating the individual degrees of freedom. By materializing these basic technical measures the device can be used in the case of a medical application in direct contact with the patient's body, wherein impacts on the patient's body detrimental to the patient can be largely excluded.

In other words, the consideration underlying the invention is to identify those degrees of freedom of robotics or a guiding device which can be integrally encased or enclosed at the guiding device) without restricting the function of the device, that is to say the robotic motions with respect to the identified degrees of freedom take place in an individual housing internal to the guiding device or within an internal enclosure so as to reduce the number of degrees of freedom freely accessible from outside and thus to reduce the risk of injuries by the robotics on the whole. Depending on the selection of the degrees of freedom provided for internal encasing/enclosure, a risk of collision of the remaining free degrees of freedom can be further reduced. That is, it is preferred to (internally) encase/enclose those degrees of freedom holding special risks for an operator, or in the case of medical application, for a patient.

Moreover, at least selected degrees of freedom additionally or alternatively can be designed to be substantially forceless. That is, the risk of a collision/injury caused by a degree of freedom of robotics is only as high as the force required to activate/actuate the degree of freedom. This force depends on the load acting on an actuator (motor drive) of the degree of freedom. It is resulting as a consequence of this consideration to minimize the operating load by accepting, outside or while bypassing the drive, unnecessary loads acting on the drive such as internal loads of the robotics itself. In this case the drive can be designed substantially only to overcome inertia forces.

More concretely speaking, the given object is achieved by robotics, preferably a (magnetic) guiding device for an intracorporeal object comprising a motor-driven positioning device (robot arm system preferably according to the articulated-arm and/or SCARA-type principle) which has a maximum of three degrees of freedom to be activated for a preferably translational motion of a connecting interface of the positioning device to which a (magnetic) end effector having a maximum of two degrees of freedom to be activated for a preferably rotational motion of a magnetic field generator is connected or connectable. The term "degree of freedom" in the present case relates to an articulation/hinge/extension etc. preferably for realizing a motion in one single plane. In accordance with the invention, at least either of the two degrees of freedom of the magnetic end effector (or both) is encased or enclosed in a (single) effector housing and/or grid frame.

That means that in case that only one degree of freedom is encased/enclosed, the magnetic field generator inside said housing/frame performs a motion in one plane (according to one degree of freedom) which does not get outside or is shielded to the outside. The second (exposed) degree of freedom then necessarily means a motion of the housing/frame itself (performed in one plane) and along with the same an equal/joint (co-) movement of the magnetic field generator. It is advantageous, however, to encase/enclose the two (rotational) degrees of freedom of the end effector or the magnetic field generator in one single housing/frame and thus to isolate/shield them to the outside. In this case the (only) housing/frame of the end effector would be moved in a translational (three-dimensional) manner exclusively by the robotics of the positioning device. A pivoting of the housing about one of its axes triggered by the positioning device is not provided. This design helps to reduce risks of unintended collision with a nearby operator during operation of the robotics or the guiding device, because the number of the degrees of freedom/movements exposed to the outside is reduced.

An additional or independent aspect of the invention provides that the three degrees of freedom of the positioning device (exclusively) permit a translational motion of the connecting interface in X-, Y- and Z-direction of a space coordinate system (degrees of freedom a, b and c) in which the Y-axis is preferably orientated substantially along the direction of gravity. In addition, axes A and B internal to the magnetic field generator are determined which, together with the polarization axis (C-/longitudinal axis), describe the orientation of the magnetic field generator relative to the space coordinate system (X-, Y- and Z-axis).

Each of the two (technically reasonable) degrees of freedom of the end effector permits a rotational motion of the magnetic field generator about an axis A and B of the relative coordinate system (A-, B- and C-axis), said axis B being preferably orientated substantially horizontally and normal to the polarization axis (C-axis) of the magnetic field generator so that a rotational motion of the magnetic field generator about the axis B causes "pitching" of the polarization axis (degree of freedom e), and wherein, independently of the current orientation of the axis A (due to pitching) a rotational motion of the magnetic field generator about the axis Y of the space coordinate system causes "pivoting" (or yawing) of the magnetic field generator (and thus of the magnetic field) (degree of freedom d).

If in the case of an extreme pitching motion the axis of polarization is co-linear with respect to the axis Y, a rotational motion of the magnetic field generator about the axis Y causes no more substantial change of the magnetic field.

In order to express the above-mentioned technical context once again in different form, hereinafter a 0-position (corresponding e.g. to a horizontal orientation) of the magnetic field generator shall be contemplated:

As explained in the foregoing, the three degrees of freedom of the positioning device permit (exclusively) a translational motion of the connecting interface into a X-, Y- and Z-direction of a space coordinate system in which the Y-axis is orientated preferably substantially along the direction of gravity and the Z-axis is accordingly orientated along the longitudinal and thus polarization axis of the magnetic field generator in the case of its horizontal position in space (0-position), whereas each of the (exclusively) two degrees of freedom of the end effector permits a rotational motion of the magnetic field generator about a respective axis, preferably about the Y-axis and the X-axis so as to cause yawing and pitching of the magnetic field generator with respect to the space coordinate system.

That is to say, there is determined a space coordinate system for the guiding device in which the Z-axis corresponds to the polarization axis and thus the longitudinal axis of the magnetic field generator in the 0-position thereof, whereas the Y-axis represents the vertical axis (preferably along the direction of gravity) and the X-axis represents the horizontal axis of the magnetic field generator. Based on said 0-position, the magnetic field generator then can be rotated about the Y- and X-axes, while a rotation of the magnetic field generator about the Z-axis (axis of polarization) is theoretically possible but is not provided, because no changes of the magnetic field occur hereby (i.e. technically meaningless).

This measure of displacing the rotational degrees of freedom exclusively to the end effector according to the above description facilitates the motion pattern of the positioning means to merely translational motions of the connecting interface that can be expected or more easily foreseen by an operator. The rotational motions superposing the former are separated from the positioning device and are at least partially encased/enclosed. Thus the motor activity exposed to the outside (motion dynamics) of the guiding device remains manageable.

An alternative advantageous configuration of the invention provides that each of the two degrees of freedom of the end effector permits a rotational motion of the magnetic field generator about the one axis A and the one axis B, the axis B being orientated substantially horizontally and vertically with respect to the axis of polarization of the magnetic field generator so that a rotational motion of the magnetic field generator about the axis B causes "pitching" of the polarization axis (degree of freedom e), and the axis A being substantially normal both to the axis B and to the axis of polarization of the magnetic field generator so that a rotational motion of the magnetic field generator about the axis A causes "yawing" of the axis of polarization of the magnetic field generator (degree of freedom d). A rotational motion of the magnetic field generator about the polarization axis is theoretically possible even in this case, but it is not provided because no substantial change of the magnetic field occurs hereby (i.e. technically meaningless). The advantages of this variant are the same as described before so that in this context the foregoing text passages can be referred to.

Another or additional aspect of the invention relates to the special design of the drive to the effect that the positioning device includes a number of motor-driven extensions or arms, at least selected extensions or arms of which are weight-balanced with respect to each of the corresponding motor drives especially in the case of articulated-arm robotics. For this purpose, preferably such balancing system is provided which performs or causes a dynamic or at least stepped adaptation (approach) of the weight balancing to the weight load currently acting upon the respective motor drive.

For example in the case of a pivoting extension/arm the static load of the drive is dependent on the current angle of inclination of the extension relative to the direction of gravity. That is, with a horizontal extension a drive is maximally weight-loaded. It is obvious that the driving force must be that high so as to ensure a movement of the extension and of loads provided on the same from each angular position. Consequently, this drive would be oversized relative to an angular position different from the horizontal orientation and therefore would be basically capable of injuring a person. As soon as the extension is so-to-speak weightless (balanced), the drive only needs to overcome the mass inertia. Hence it can be designed to be definitely smaller/weaker.

Hence it is advantageous when the positioning device includes a number of motor-driven extensions or arms, at least selected extensions or arms of which are supported relative to the corresponding motor drives such that the motor drives do not have to carry or overcome any static weight load. Basically this can be achieved by using a counteracting force system (e.g. attaching counter-weights and/or springs to lever arm kinematics etc.) or by the predetermined direction of movement of the extensions preferably pointing substantially normal to gravity (according to the principle of SCARA robotics). In the latter case the static weight force would be carried by an appropriately designed movable bearing in parallel to the drive, thereby relieving the drive itself.

According to another or additional aspect of the invention, the respective motor drive is limited as to its driving force for selected degrees of freedom (e.g. by disposing an safety-friction clutch, a safety clutch, a step motor that falls out of synchronism at a particular force, a pressure relief valve etc.) so that the driving force to be maximally output is equal to or greater than an operating load force to be expected but equal to or smaller than a predetermined maximum force at which injury of a patient or an operator in the case of collision is largely excluded. Such maximum force is defined already in prior art according to EN ISO 10218, which is incorporated by reference in its entirety, for instance, so that the respective standards can be referred to in this context.

Irrespective of the afore-described safeguarding systems/measures it would be advantageous to provide a monitoring means to which a number of sensors for monitoring the operating state of the guiding device and for turning off the guiding device, where appropriate, in the case of a detected predetermined risk of accident is connected or connectable. Preferably the sensors are selected/selectable from a group of sensors comprising:

- a force sensor for detecting the drive load on the respective (selected) drive,
- a touch sensor for detecting the contact force between the magnetic end effector or a selected extension of the positioning device and an operator or a patient,
- a deformation detecting sensor for detecting e.g. an indentation preferably at the end effector housing,
- an optical sensor for optical detection of obstacles and
- a distance sensor for detecting a distance from an obstacle.

As an alternative or in addition to this, the magnetic guiding device can also be equipped with motion limiting means preferably in the form of programmable and/or mechanical limit stops/limit switches mounted to the positioning device and/or the magnetic end effector so that at least a selection of the maximum of three degrees of freedom of the positioning device and/or the maximum of two degrees of freedom of the magnetic end effector is mechanically limited to a predetermined motion range.

As already indicated in the foregoing, the housing of the magnetic end effector is to remain advantageously unchanged as regards its orientation. In this case the housing of the magnetic end effector preferably points always substantially in the direction of gravity independently of the current movement of the positioning device and/or of the magnetic field generator. In other words, the magnetic field generator is supported inside the housing/frame of the end effector so that the yaw axis thereof in the 0-position (normal to the now horizontal polarization axis) points to the direction of gravity. This has the advantage that an operator need not pay attention to any protruding movement/pivoting of the housing itself, whereby the risk of injury is further reduced.

BRIEF DESCRIPTION OF THE DRAWING FIGURES

Hereinafter the invention will be illustrated in detail by way of preferred embodiments with reference to the accompanying figures.

Figure 2:
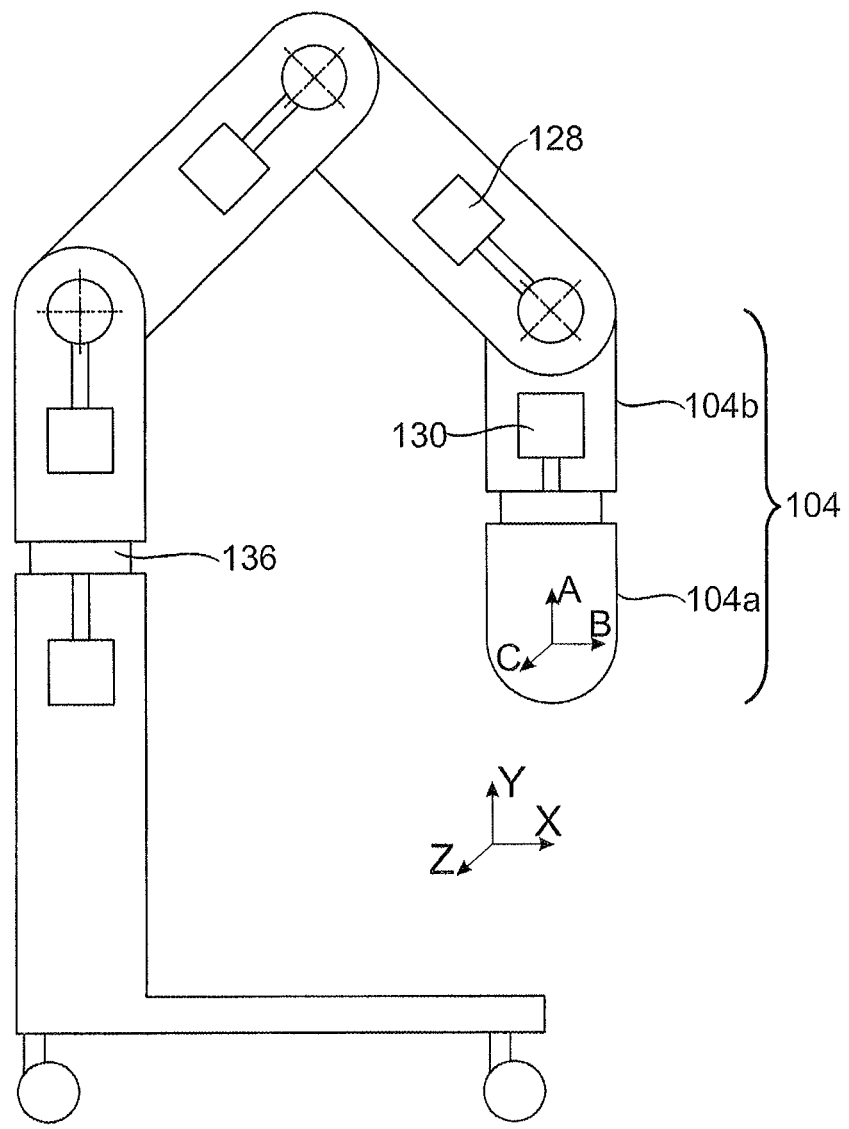
Figure 3:
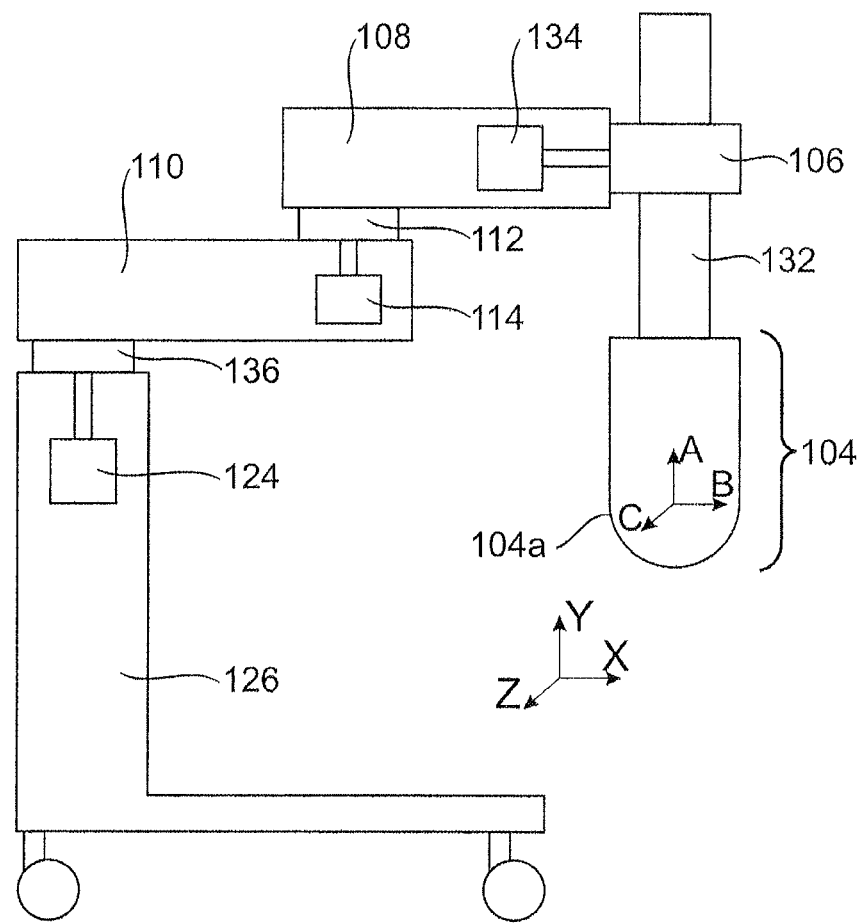
Figure 4:
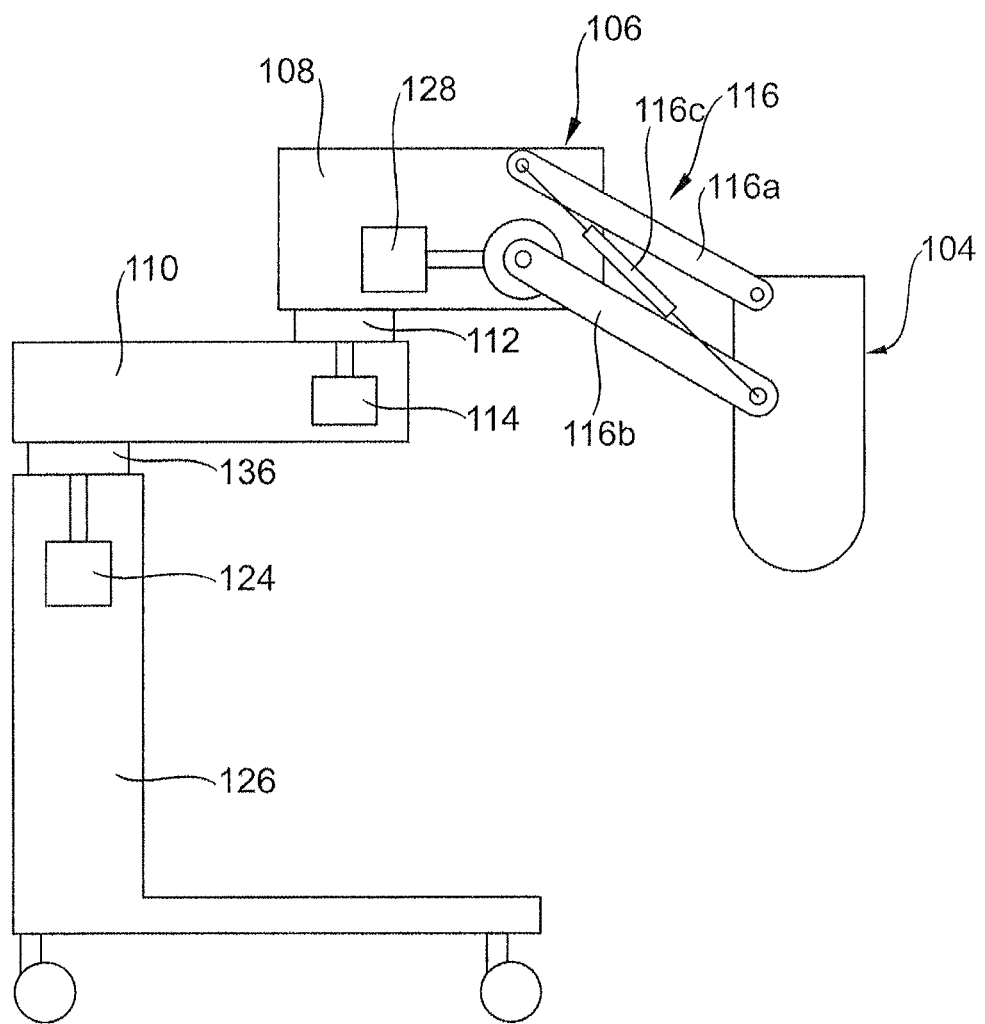
Figure 5:
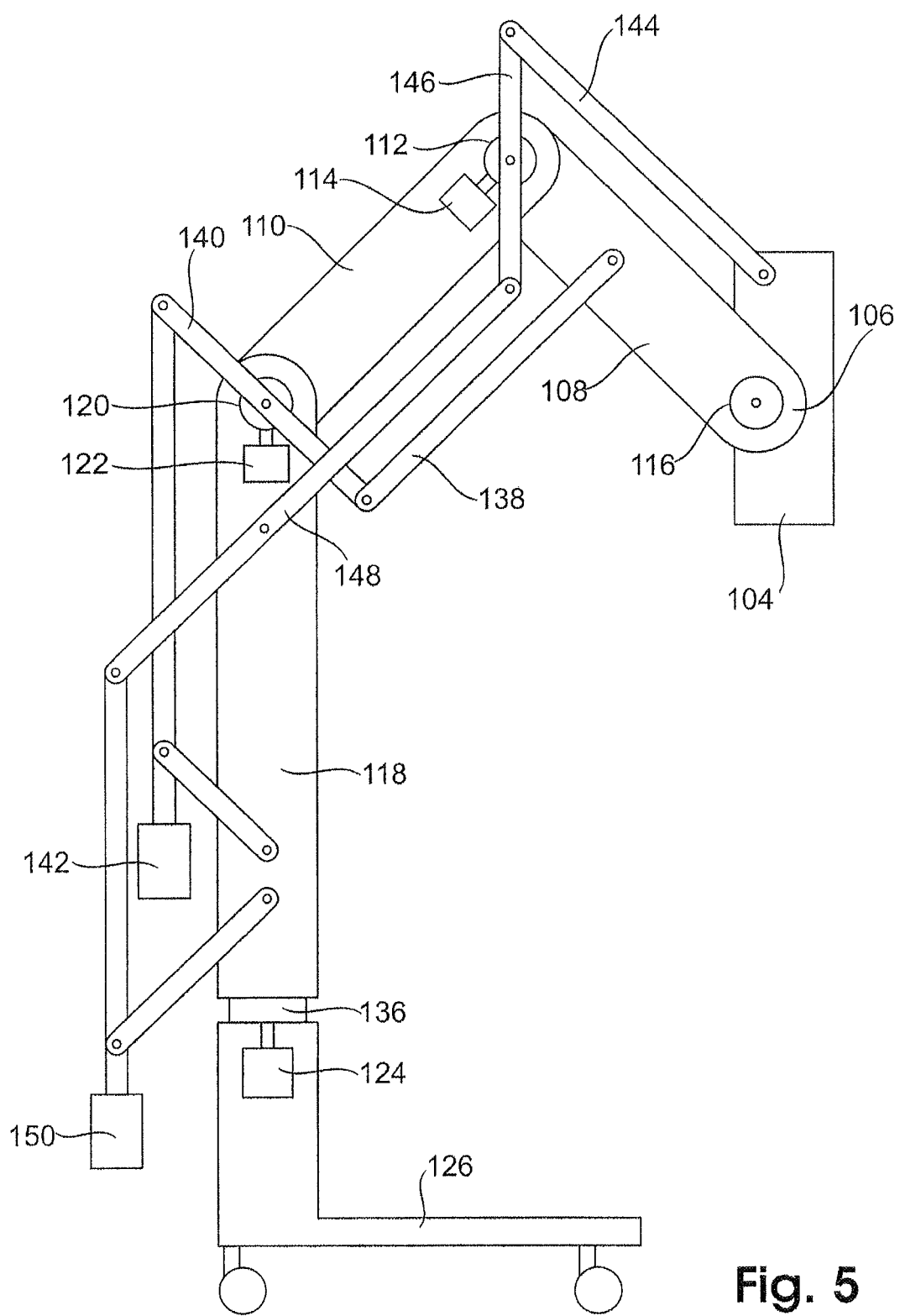
Figures 7A, 7B:
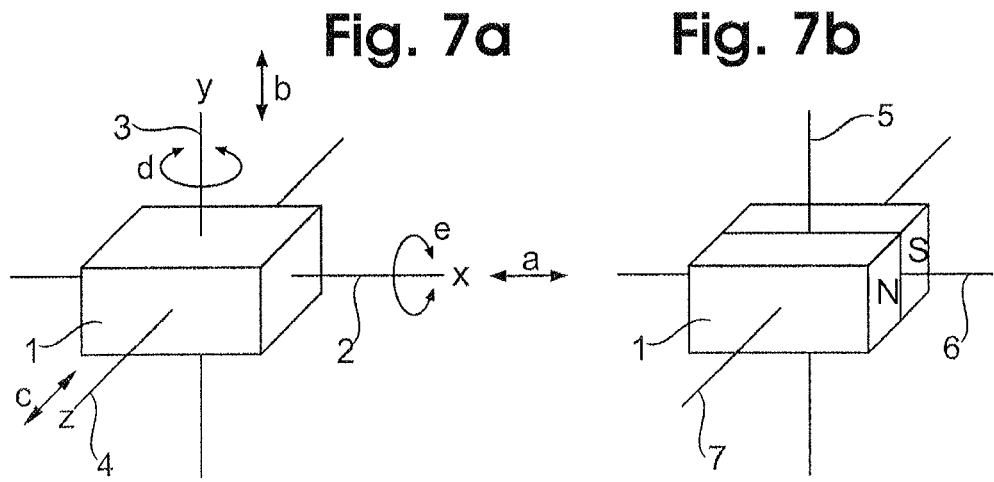
Figure 8:
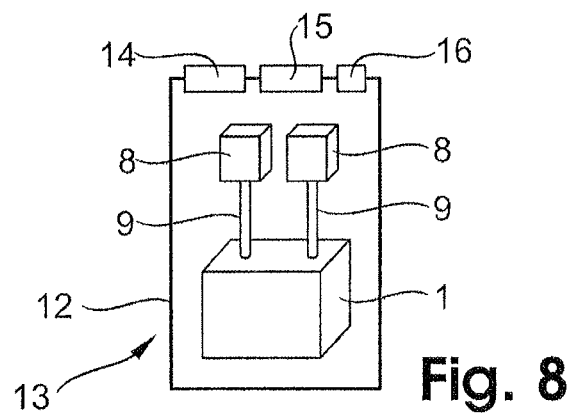
Figure 9:
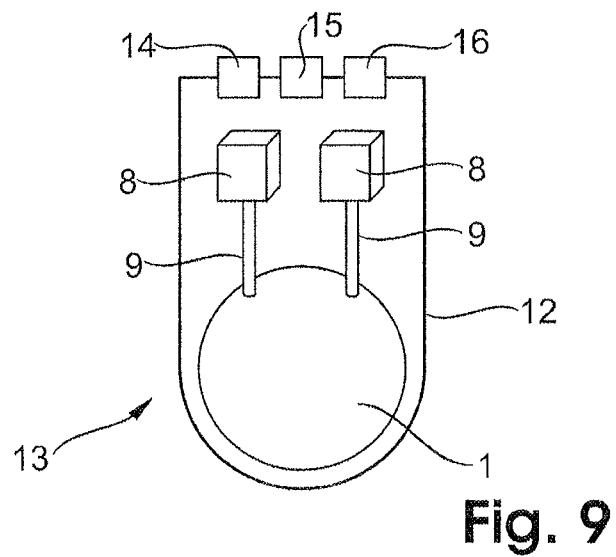
Figure 11C:
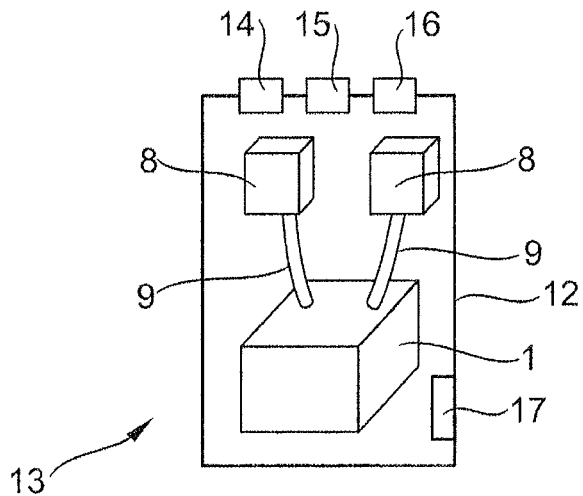
Figure 12:
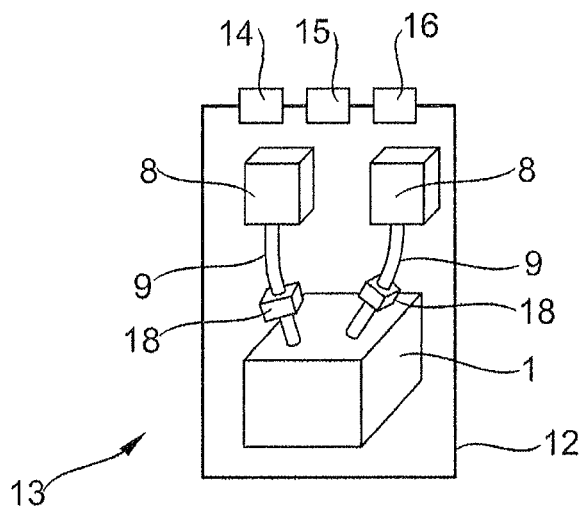
Figure 13:
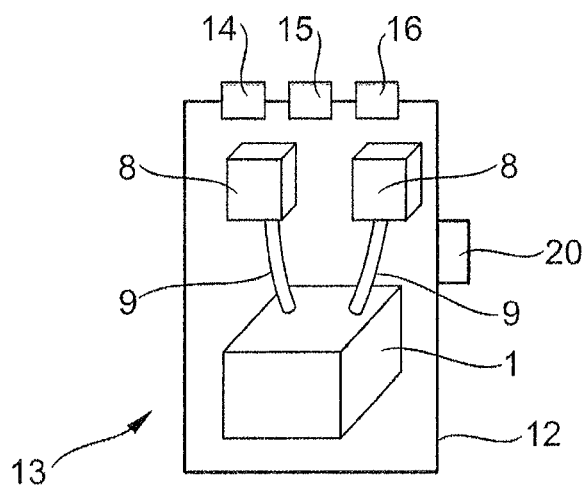
Figure 17A:
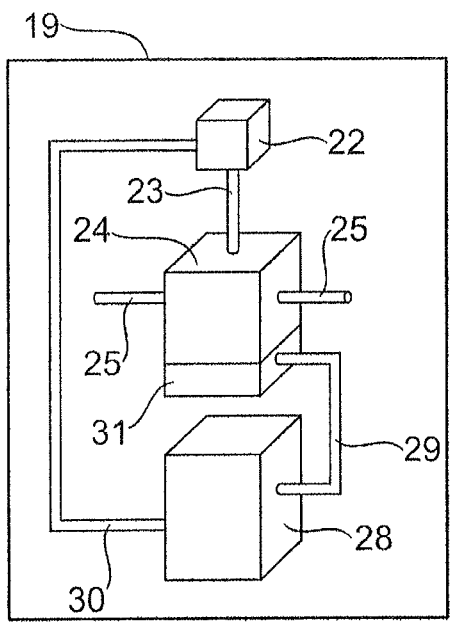
Figure 17B:
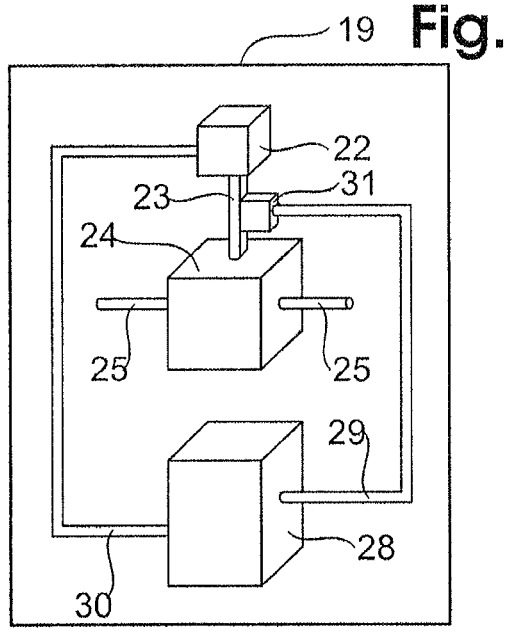
Figure 18A:
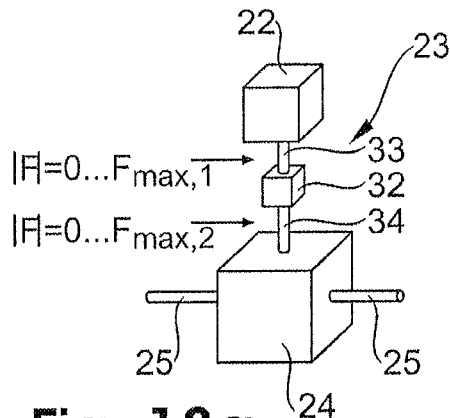
Figure 17C:
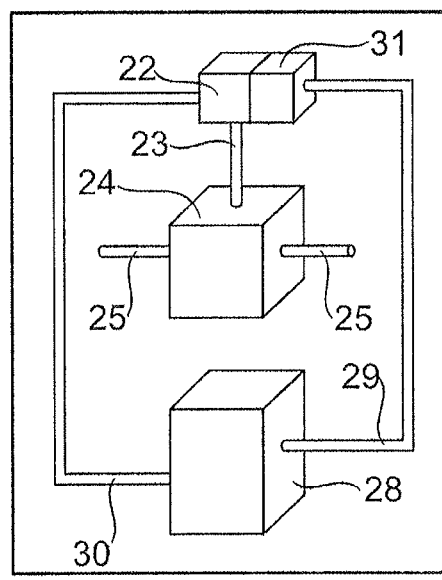
Figure 18B:
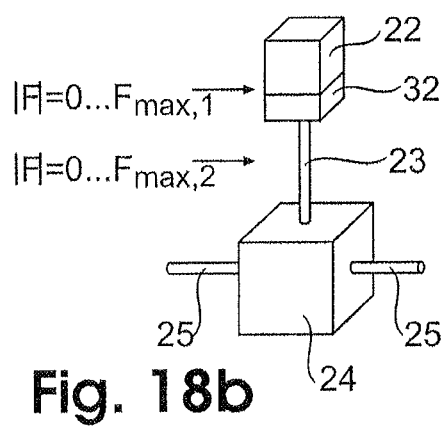
Figure 18C:
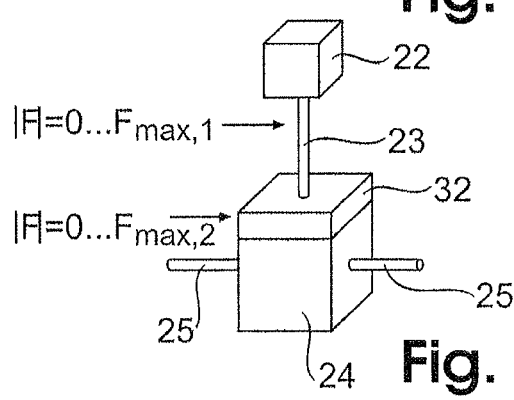

FIG. 1 shows the basic design principle of a (magnetic) guiding device or a (medical) robot arm according to a first preferred embodiment of the invention including the encasement of two selected degrees of freedom (a degree of freedom corresponds to the definition according to aspects of the invention of an articulation or hinge to obtain a one-dimensional movement or rotation about an axis), FIG. 2 shows the basic design principle of a (magnetic) guiding device or a (medical) robot arm according to a second preferred embodiment of the invention as an alternative to the embodiment according to FIG. 1 including the encasement of one single selected degree of freedom, FIG. 3 shows the basic design principle of a (magnetic) guiding device or a (medical) robot arm according to a third preferred embodiment of the invention including the encasement of one (single) selected degree of freedom as well as including a structural robot arm arrangement with minimized load of the actuating elements by its dead weight, FIG. 4 shows the basic design principle of a (magnetic) guiding device or a (medical) robot arm according to a fourth preferred embodiment of the invention including the encasement of two selected degrees of freedom as well as including a structural robot arm arrangement with minimized load of the actuating elements by its dead weight and additionally or alternatively a weight-balanced (substantially dynamically balanced) robot arm arrangement, FIG. 5 shows the basic design principle of a (magnetic) guiding device or a (medical) robot arm according to a fifth preferred embodiment of the invention comprising a substantially dynamically balanced robot arm arrangement for use e.g. in one of the embodiments according to FIGS. 1 and 2, FIG. 6 shows a table of forces for comparison of a robot arm design having substantially vertical axes of rotation of the individual arms, a robot arm design having substantially horizontal axes of rotation of the individual arms and a robot arm design having substantially horizontal axes of rotation as well as a dynamic balancing (weight compensation), FIG. 7a-7b show respective schematic diagrams of a magnetic field generator (permanent magnet) for defining the five degrees of freedom to which it is to be maximally movable by means of the positioning device according to aspects of the invention (of FIGS. 1 through 5) and of the end effector connected thereto, FIG. 8 shows the magnetic end effector including the magnetic field generator supported therein with its basic functions, FIG. 9 shows the magnetic end effector having the basically structural design of a magnetic field generator of the end effector, FIGS. 10a-10e show a plurality of alternative forms for a magnetic field generator according to aspects of the invention as it can be mounted in the end effector, FIGS. 11a-11c each shows a magnetic end effector including housing as well as a sensor system differently attached thereto, FIG. 12 shows a further magnetic end effector including a sensor system between the drive (actuator) and the magnetic field generator, FIG. 13 shows another magnetic end effector including housing as well as an operating panel disposed thereto, FIG. 14 shows the schematic diagram of a positioning device according to aspects of the invention for activating exclusively translational degrees of freedom (according to FIGS. 1-5) including a connecting interface for a magnetic end effector according to any one of the FIGS. 7 through 13, FIGS. 15a-15c show the positioning device and, respectively, a moving part of the positioning device comprising an individually encased arm and an actuator including sensors differently attached thereto (to the housing), FIG. 16 shows the positioning device and, respectively, a moving part of the positioning device comprising an individually encased arm and an actuator including an operating panel attached thereto (to the housing), FIGS. 17a-17c show different basic configurations for an actuator-connecting element-articulation-unit according to aspects of the invention, FIGS. 18a-18c show alternative basic configurations for an actuator-connecting element-articulation-unit according to aspects of the invention and FIGS. 19a-19f show alternative configurations for actuators according to aspects of the invention for actuating degrees of freedom of the positioning device and/or of the magnetic end effector.

DETAILED DESCRIPTION OF THE DRAWING FIGURES

Positioning Device

FIG. 1 schematically shows a first embodiment of a magnetic guiding device 100 according to aspects of the invention. Accordingly, the guiding device 100 initially consists of a positioning device (robot arm system) 102 and a magnetic end effector 104 connected to a connecting interface 106 of the positioning device 102.

The positioning device 102 of the first embodiment of the invention includes two pivot arms 108, 110 serially hinged to each other whose (substantially horizontally orientated) connecting hinged joint 112 can be motor-activated (via the actuator 114). At the free end of the one (free) pivot arm 108 the connecting interface 106 is hinged by means of a further horizontal hinge 116, whereas the free end of the other (integrated) pivot arm 110 is pivotally hinged to a rotating arm 118 likewise by means of a horizontal hinge 120. Also this hinged joint 120 arranged between the other (integrated) pivot arm 110 and the rotating arm 118 can be motor-activated (via the actuator 122). The rotating arm 118 is finally pivoted on a base 126 about its longitudinal axis (vertically) by motor-drive (via the actuator 124), the base being supported on rollers in the present case so as to be able to be preferably manually displaced.

This arm/extension-articulation mechanism enables the positioning device 102 to move the connecting interface 106 in a translational three-dimensional manner. That is, the positioning device 102 according to the first preferred embodiment of the invention has exclusively three degrees of freedom to be reasonably activated, viz. for a translational motion of the connecting interface 106 in the X-, Y- and Z-direction of a space coordinate system (to be defined at will, but preferably with the Y-axis along the direction of gravity).

In the present case the magnetic end effector 104 is mechanically and electrically (pneumatically and/or hydraulically) docked to the connecting interface 106 which is supported at the one (free) pivot arm 108 via the horizontal hinge 116 adapted to be motor-activated (via the actuator 128). As will be explained in detail hereinafter, said hinge 116 is preferably activated so that the magnetic end effector 104 always points in a particular direction with respect to the vertical and further preferably is (always) orientated in the vertical direction. As an alternative to this, it is also possible, however, that the horizontal hinge 116 between the connecting interface 106 and the magnetic end effector 104 has no motor drive so that the magnetic end effector 104 always orientates itself vertically exclusively due to the gravity acting upon the same independently of the current orientation of the positioning device 102.

In the case of the embodiment according to FIG. 1, the magnetic end effector 104 includes one single effector housing 104a which is fixedly connected mechanically and electrically (pneumatically and/or hydraulically) to the connecting interface 106 and thus points vertically downwards (with respect to the connecting interface 106) (i.e. is arranged below the connecting interface 106). Inside the single effector housing 104a a magnetic field generator 1, which is not shown in detail in FIG. 1 but will be described in more detail hereinafter, is accommodated whose support in the present case has exactly two degrees of freedom to be reasonably activated, i.e. for "pitching" and "pivoting/yawing" of the magnetic field generator 1 relative to a space coordinate system.

The terms "pitching" and "yawing" basically originate from aeronautical engineering and there describe the movement of a flying object related to the coordinate system internal to the flying object. However, in the present description the movements of "pitching" and "yawing" are to be related to the space coordinate system.

In accordance with the embodiment of FIG. 1, the two degrees of freedom (or hinges/articulations) for "pitching" (degree of freedom e) and "pivoting" or "yawing" (degree of freedom d) of the magnetic field generator 1 according to the above definition are encased/housed in the effector housing 104a and thus no longer accessible from outside. In this case the effector housing 104a moves quasi integrally with the connecting interface 106 in a substantially merely translational manner into the afore-denoted X-, Y-, Z-directions of the positioning device 102, wherein the rotational motions of the magnetic field generator 1 for the pitching and pivoting or yawing motion thereof are performed within the effector housing 104a which is preferably always vertically orientated.

In this context, the term "vertically orientated effector housing" is defined as follows:

As shown in FIG. 1, the housing has a rounded outer contour at a lower (in the direction of gravity) end portion. Said contour constitutes a so called contact side/face for contacting a patient's body. Said contact side is preferably always provided at the lower side (viewed in the direction of gravity) of the housing and thus defines the vertical orientation of the housing. It is also referred to the fact, however, that the contact side can as well be the vertical side (according to the foregoing definition), for example when a patient adopts an upright or sitting position instead of a horizontal position.

FIG. 2 shows an alternative to the embodiment according to FIG. 1 in which the positioning device 102 has a structural design as already described by way of FIG. 1 above. What is different, however, is the configuration of the magnetic end effector 104 which in this case includes two housings 104a, 104b, the one housing 104b thereof being fixedly connected mechanically/electrically/hydraulically/pneumatically to the connecting interface 106 of the positioning device 102 and, due to the effect of gravity or actively by an appropriately driven actuator 128 (according to FIG. 2) always pointing vertically (in accordance with the above definition) downwards. At the one housing 104b mounted to the connecting interface 106 another housing 104a is pivoted by motor-drive (via the actuator 130) about the longitudinal housing axis (in this case the vertical axis). In the further housing 104a the magnetic field generator is accommodated such that it is adapted to perform a motor-driven pitching motion with respect to the longitudinal housing axis. In the present case, the yawing motion of the magnetic field generator is thus performed by a motor-driven rotation of the further housing 104a while the housing 104b is idling as to rotation. That is, in the event of FIG. 2 merely the one degree of freedom (hinge) for a pitching motion of the magnetic field generator is encased/housed in the effector housing, whereas the degree of freedom (hinge/axis of rotation) for a yawing motion of the magnetic field generator effectuated by rotating the further effector housing 104b is freely accessible from outside.

In this context, the motions of the magnetic field generator 1 according to the exclusively two technically reasonable degrees of freedom are exemplified by way of FIGS. 1 and 2.

According to the preferred embodiment of the invention it is provided that the housing 104a, b is orientated so that the contact side thereof with the patient (not shown in detail) points vertically downwards. Accordingly, the external space coordinate system including the X-, Y- and Z-axis orientates itself according to the direction of gravity. That is, the Y-axis is linear with respect to the direction of gravity.

Although a home or 0-position of the magnetic field generator 1 (e.g. a permanent magnet) inside the housing 104a, b can be independent of the space coordinate system and thus of the orientation of the housing 104a, b, it is assumed by way of example that an internal polarization axis C (longitudinal axis) of the magnetic field generator 1 in 0-position extends in the Z-direction of the inserted space coordinate system (viz. extends horizontally). An internal axis A of the magnetic field generator 1 vertical hereto in 0-position then extends in the direction of gravity and an internal axis B of the magnetic field generator 1 vertical hereto in 0-position then extends likewise horizontally along the X-axis of the space coordinate system. When the magnetic field generator 1 pitches, then it rotates about the internal axis B, i.e. about the space coordinate axis X. When the magnetic field generator 1 additionally yaws, then it pivots in any case about the space coordinate axis Y, but only proportionately about the already pitched internal axis A. This proportion necessarily decreases the larger the pitch angle and finally becomes 0 when the internal axis C (polarization axis) points in the direction of gravity. Then the rotation about the Y-axis is converted to a rolling motion having no influence on the magnetic field.

It is pointed out in this context that the housing 104a, b need not necessarily be orientated along the direction of gravity but can also adopt an angle with the same. In this case, the space coordinate system and the reference axes for "yawing" and "pitching" are appropriately varied.

The embodiment according to FIG. 3 shows a positioning device 102 (robot arm system) different in design and conception from the positioning device 102 of the first and second embodiments.

In this case, the two pivot arms 108, 110 serially hinged to each other are coupled by means of a vertical hinge 112 which merely permits a horizontal relative rotation of the two pivot arms 108, 110. At its free end the one (free) pivot arm 108 is also provided with a connecting interface 106, however this time consisting of a seat for a telescopic rod 132 which can be vertically displaced inside the seat 106 by motor-drive (via an actuator 134). The telescopic rod 132 can be, for instance, a toothed rack, a piston rod or similar push rod guided to be vertically displaceable in the seat 106 of, for instance, a gearbox casing, a pressure cylinder or similar drive unit.

The free end of the other (integrated) pivot arm 110 is coupled to a foot of the preferably manually displaceable base 126 via a vertical hinge 136. This hinge 136, too, can be (motor-) activated via the actuator 124.

Finally the magnetic end effector 104 is disposed at one end (vertical lower end) of the telescopic or push rod 132. Said magnetic end effector 104 can be structured according to the principle of both the first and the second embodiment according to the foregoing description. That is, it can be formed to have a single housing or two housings rotatable against each other, wherein in the first case two degrees of freedom are encased and in the second case only one degree of freedom is encased.

It is resulting from the basic concept of the afore-described positioning devices that due to the horizontal orientation of the respective hinges the dead weight of the respective pivot arms 108, 110 and the load arranged thereon (end effector) act upon the actuating elements of the first and second embodiments, whereas in the third embodiment according to FIG. 3 (except for the connecting interface 106) said load or force is carried by the vertical hinges. That is, in the event of the third embodiment, the actuating elements substantially only have to overcome the mass inertia for moving the pivot arms 108, 110 (including the end effector 104), while in the event of the first and second embodiments the actuating elements also have to handle the load from the gravity of the pivot arms 108, 110. In order to illustrate this problem it is referred to FIG. 6 in this context.

In the central representation FIG. 6 shows the actuator force required to move a pivot arm according to the first and second embodiments. It is assumed that the actuator force is slightly greater than the actually required force and is appropriately adjusted by means of electric limiters. The actuator force is composed of the force necessary for moving the end effector e.g. for applying pressure to a patient's body as well as the gravity of the load acting thereupon (including the respective pivot arms).

In contrast, the upper representation shows the actuator force in the case of the afore-mentioned third embodiment. As is clearly visible, the actuator force is substantially reduced to the required operating force (with little surplus) including the necessary pressing force on a patient's body, because the force from the gravity of the load is carried by the vertical hinges. In this case the actuating members of the positioning device can be designed to be definitely weaker than in the first and second embodiments, thus entailing a positive effect on the safety of the entire system.

In order to render the positioning device of the first and second embodiments still safer and thus suited for medical application, the fourth embodiment of the invention according to FIG. 4 provides the use of balancing (balancing device).

In this case the positioning device 102 relates to a combination of the first three embodiments according to which concretely the two pivot arms 108, 110 of the positioning device 102 are coupled to each other and hinged to the displaceable basis 126 (i.e. via vertical hinges) in accordance with the principle of the third embodiment, whereas the magnetic end effector 104 is coupled via a horizontal hinge 116 to the connecting interface 106 of the positioning device 102 which, in this case, is force-balanced, viz. counterbalanced, however.

In detail the horizontal hinge 116 comprises a parallelogram-type articulation having at least two parallel hinge arms 116a, 116b counterbalanced via a diagonal spring 116c. The spring force is adjusted to the load of the magnetic end effector 104 so that the diagonal spring 116c substantially carries the load of the end effector. At least one of the two hinge arms 116a, 116b furthermore can be actuated via the one actuator 128 so as to vertically move the magnetic end effector 104. Since the diagonal spring 128c substantially absorbs the weight of the end of 104, the actuator 128 only has to overcome the mass inertia to move the end effector 104 and accordingly can be designed to be low-powered. This is illustrated, for example, in FIG. 6, lower representation.

As a consequence, the actuator force with little surplus can be substantially reduced to the required operating force to overcome mass inertia including the intended pressing force on a patient's body and therefore most largely corresponds to the actuator force according to the upper picture (relating to the third embodiment of the invention).

It is obvious that the balancing principle is applicable to all hinges of the positioning device 102 as is exemplified in the fifth embodiment of the invention according to FIG. 5.

The conceptual structure of the positioning device 102 shown here substantially corresponds to the first or second embodiment according to FIGS. 1 and 2. However, in this case a push rod 138 is hinged in a central portion of the one (free) pivot arm 108, said push rod being coupled to a lever arm 140 which in its central portion is articulated to the hinge 120 between the other (integrated) pivot arm 110 and the rotating arm 118. At the other end of the lever arm 140 a weight 142 is arranged (via a vertically guided pendulum rod).

Furthermore a push-pull rod 144 is hinged with the magnetic end effector 104 vertically above the horizontal hinge 116 between the end effector 104 and the connecting interface 106, said push-pull rod being coupled to a first lever rod 146 which in turn is hinged to the horizontal hinge 112 between the two serial pivot arms 108, 110. At the other end of the first lever rod 146 a tie rod 148 is coupled which is pivoted in a central portion of the rotating arm 118 and at the other end is provided with a weight 150 (via a vertically guided pendulum rod). It is noted in this context that, except for the hinge 116 between the magnetic end effector 104 and the connecting interface 106, all other hinges/axes of rotation can be (motor-) actuated, whereas the magnetic end effector 104 is always vertically orientated via the tie and lever rods 14, 146, 148. The afore-described lever mechanics as well as the weights are designed so that the actuators are substantially forceless independently of the pivoting position of the pivot arms 108, 110 and therefore have to be designed only to overcome the mass inertia.

Summing up it is stated in this context that by housing selected degrees of freedom (hinges or articulations) in appropriate housings, in the present case by encasing the rotational degrees of freedom of the magnetic field generator in the effector housing, the number of the freely accessible degrees of freedom (hinges) and of the pivoting motions of elements of the magnetic guiding device coupled thereto can be reduced, whereby the risk of injury of an operator and/or a patient can be reduced while maintaining the required functions. Since, moreover, due to the special orientation of the hinges between the pivot arms (vertical) and/or the counterbalancing of the hinges (horizontal) the actuating elements have to be designed only to overcome forces of inertia, the maximum forces achievable hereby can be reduced so far that they are no more sufficient to injure an operator or a patient. The use of either of the two afore-mentioned measures already suffices to fulfill the given task, wherein the combination of both measures further improves the safety characteristic of the magnetic guiding device on the whole.

Hereinafter the magnetic end effector according to aspects of the present invention will be basically described in detail.

Magnetic End Effector

The magnetic end effector 13 according to FIG. 8 is a device that actuates at least one rotational degree of freedom (degree of freedom d or e) but preferably both rotational degrees of freedom (degrees of freedom d and e) of a magnetic field generator 1 according to FIGS. 7a and 7b. This case preferably concerns a respective rotation of the magnetic field generator 1 in 0-position about the axis A (in 0-position corresponds e.g. to the Y-axis of a space coordinate system) substantially along the gravity for pivoting or yawing as well as rotation of the magnetic field generator 1 about the axis B (corresponding e.g. to the X-axis of the space coordinate system) normal to the polarization axis/longitudinal axis of the magnetic field generator 1 for pitching. The axes A and B are described in the foregoing so that in this context the respective text passage can be referred to. A rotation of the magnetic field generator 1 about the polarization axis C (rolling) is ruled out with this definition according to FIG. 7a, because this would not substantially vary the magnetic field.

Actuation of the degrees of freedom is performed within a housing 12 of the magnetic end effector 13 so that the actuation does not result in a change of position, orientation or shape of the magnetic end effector 13 (of the housing 12). In the embodiment according to FIG. 8 (corresponding to the end effector according to FIG. 1) preferably no surface parts or components of the housing 12 are moving.

To this effect, the magnetic end effector 13 has at least one actuator 8 which is coupled via a respective transmission element 9 to the magnetic field generator of compact design 1 such that selectively actuation of the degree of freedom d or actuation of the degree of freedom e can be obtained. This actuation is detected from the outside (outside the housing 12) preferably only by observing a rotation of the magnetic end effector and, respectively, the housing 12 to be caused via an external actuator about the degree of freedom not actuated inside the housing 12 and in each case by a varying orientation of the magnetic field. This corresponds to the end effector according to FIG. 2.

In an advantageous configuration of the magnetic end effector 13 according to FIGS. 8 and 9 the magnetic end effector 13 includes two actuators 8 each of which is coupled via a transmission element 9 to the magnetic field generator of compact design 1 such that both an actuation of the degree of freedom d and an actuation of the degree of freedom e can be obtained inside the housing 12. This actuation is detected from the outside (outside the housing 12) only by monitoring an orientation of the magnetic field, whereas the housing 12 performs no rotational motion.

In an advantageous configuration of the transmission element 9 according to FIG. 12 the/each transmission element 9 includes a sensor element 18 collecting information which allows conclusions at least about the position of the magnetic field generator of compact design 1. These sensor elements 18 can be, for instance, motion, position or force sensors.

In an advantageous configuration of the transmission element 9, thus the transmission element 9 is provided with a (further) sensor element 18 collecting information which allows conclusions at least about the force acting on the magnetic field generator of compact design 1.

The essential feature of the structural design of the magnetic end effector 13 is that the actuators 8 as well as the transmission elements 9 are provided inside the housing 12 of the magnetic end effector 13. The central advantage of this structural design of the magnetic end effector 13 resides in the fact that the actuation of the degrees of freedom d and/or e of the magnetic field generator of compact design 1 does not result in any motions of the magnetic end effector 13 relevant to a patient's safety.

The magnetic end effector 13 has a connecting element 14 for the transmission of forces. The connecting element 14 serves for the orientation of the magnetic end effector 13 in space (preferably in the vertical direction) by introducing holding forces or forces for accelerating the magnetic end effector 13.

The magnetic end effector 13 further has a connecting element 15 for the transmission of energy. Such energy is used at least for operating the actuators 8. In an advantageous configuration of the connecting element 15 preferably electrical energy is transmitted via the connecting element 15. This configuration has the advantage that, apart from the actuators 8, also electronic components provided in the magnetic end effector can be operated by the electrical energy. In a further advantageous configuration of the connecting element 15 preferably pneumatic or hydraulic energy is transmitted via the connecting element 15.

Finally, the magnetic end effector 13 has a connecting element 16 for the transmission of data. All said connecting elements 14, 15, 16 are connectable or connected to a connecting interface of the positioning device.

In an advantageous application scenario the magnetic end effector 13 is guided only above the preferably horizontal patient's body. In connection with the control principle of an intracorporeal magnetic object disclosed in EP 2 347 699 A1, which is incorporated by reference in its entirety, the magnetic end effector 13 always has to be positioned above an intracorporeal object to be controlled (not shown in detail). Thus the lower side of the magnetic end effector 13 provided as contact side preferably points in the direction of the patient, i.e. downwards.

In an advantageous configuration of the magnetic end effector 13 the lower side of the housing 12 preferably facing the patient's body therefore has a rounding which preferably exhibits a hemispherical shape. Moreover, according to the same advantageous configuration of the magnetic end effector 13 the magnetic field generator of compact design 1 is formed to have a compact shape. In an advantageous configuration of the magnetic field generator of compact design 1 having a compact shape it is in the form of a cuboid (FIG. 10a). In another advantageous configuration of the magnetic field generator of compact design 1 having a compact shape it is in the form of a cube (FIG. 10b). In another advantageous configuration of the magnetic field generator of compact design 1 having a compact shape it is formed as a cylinder (FIG. 10c). In a further advantageous configuration of the magnetic field generator of compact design 1 having a compact shape it is formed as a cylinder having chamfered or rounded edges (FIG. 10d). In a further advantageous configuration of the magnetic field generator of compact design 1 having a compact shape it is formed as a sphere (FIG. 10d). In another advantageous configuration of the magnetic field generator of compact design 1 having a compact shape it is formed as any other geometrical shape which is advantageous to a compact design.

The advantage of said advantageous configurations of the magnetic end effector 13 resides in the fact that by rounding the lower side of the housing 12 preferably facing the patient's body and fitting the magnetic field generator of compact design 1 into the form of the lower side of the housing 12 by imparting a compact shape to the magnetic field generator 1, the magnetic field generator 1 can be approached as closely as possible to the intracorporeal object to be controlled, while simultaneously the actuation of the two degrees of freedom d and e inside the housing 12 is not impaired. This applies in particular to maneuvers in which the magnetic end effector 13 is pressed onto the patient's body with a defined force so as to be positioned as closely as possible to the intracorporeal object to be controlled.

In an advantageous configuration of the housing 12 according to FIGS. 11a to 11c the housing 12 includes at least one sensor element 17. Said at least one sensor element 17 is used to detect forces acting on the housing 12 that have occurred due to collisions.

In an advantageous configuration of the at least one sensor element 17 said sensor element 17 is a deformation sensor which is connected to the housing 12 such that it can record deformations in a delimited area of the housing 12 and thus the force introduced to the housing can be concluded therefrom.

In an advantageous configuration of the at least one sensor element 17 said sensor element 17 is a force sensor which is connected to the housing 12 such that, as connecting element between two elements of the housing 12, it can record a force introduced from outside which acts upon either of the elements.

In an advantageous configuration of the at least one sensor element 17 said sensor element 17 is a mechanical switch which is connected to the housing 12 such that it acts as a connecting element between two elements of the housing 12 and a force introduced from outside which acts upon either of the elements results in actuation of the sensor element 17.

In an advantageous configuration of the at least one sensor element 17 said sensor element 17 is a force-sensitive element arranged at the outside of the housing 12 such that contact forces acting on the sensor element 17 are recorded.

In an advantageous configuration of the housing 12 according to FIG. 13 the housing 12 includes an operating element 20 (in addition to said sensors).

In an advantageous configuration of the operating element 20 said operating element 20 has at least one handle that permits manual operation of the magnetic end effector 13 while bypassing/overcoming the actuating elements of the positioning device.

In a further advantageous configuration of the operating element 20 said operating element 20 includes at least one touch-sensitive switch for manual activation of individual actuators of the positioning device.

In a further advantageous configuration of the operating element 20 said operating element 20 includes at least one optical display element, for example for representing virtual motion barriers of the positioning device according to the foregoing introductory part of the description.

Positioning Device for Orientation of the Magnetic End Effector According to the Foregoing Description The positioning device 21 for orientating the magnetic end effector 13 according to FIG. 14 (cf. system line 21 in FIG. 14) has the function of positioning the magnetic end effector 13 in space (space coordinate system). The magnetic end effector 13 according to the afore-described preferred design is adapted to control the degrees of freedom d and e of the magnetic field generator of compact design 1. Hence it is the object of the positioning device 21 to position the magnetic end effector 13 along the degrees of freedom a, b and c. In this way, the magnetic field generator of compact design 1 can be orientated into all five degrees of freedom a through e required (reasonable) for the control of intracorporeal objects by the combination of the positioning device 21 and the magnetic end effector 13 (which jointly form the guiding device).

The positioning device 21 moves the magnetic end effector 13 (in a translational manner) in space. These motions can lead to a collision with and an action of force upon the patient's body as this was already described in the beginning, wherein certain collisions or actions of force may even be intended. The structural design of the positioning device 21 as well as the actuation thereof therefore are configured, according to aspects of the invention, so that a collision with and an action of force upon the patient's body cannot lead to impacts on the patient's body endangering the patient. Preferably the structural design of the positioning device 21 and the actuation thereof are configured, according to aspects of the invention, so that even in the case of incorrect operation or malfunction of one or more components of the positioning device no impacts on the patient's body endangering the patient can occur.

The positioning device 21 is provided with at least three actuators 22, as this has been described already by way of FIGS. 1 through 5, each of which is connected via a transmission element 23 to a respective articulation (hinge in horizontal or vertical orientation) 24. The term "articulation" comprises both rotational articulations/hinges and linear guides (telescopic rods, toothed racks, piston/cylinder arrangements etc.) or a number of chain links. The design is such that an actuator 22 is connected to the respective articulation 24 via the respective transmission element 23 such that the actuator 22 is capable of actuating the respective articulation 24.

The actuator 22 can be configured as rotational actuator e.g. according to the design of an electric motor, or as linear actuator e.g. according to the design of a fluidic lift cylinder.

The positioning device 21 includes a connecting element 26 (corresponding to the afore-described connecting interface comprising the terminals for the connecting elements 14 to 16 of the end effector 13) for the transmission of forces and energy as well as for mechanical coupling of the positioning device 21 to the magnetic end effector 13.

The positioning device 21 moreover includes a fastening element 27 which serves for stationary fixing of the positioning device 21 in space. In an advantageous configuration of the fastening element 27 said fastening element 27 is formed as the base according to FIGS. 1 to 5 which can be selectively locked or displaced in space, for instance, by lockable rollers. In a further advantageous configuration of the fastening element 27 said fastening element 27 includes at least one device suited for fixation to an object, for example the examination couch.

The positioning device 21 moreover includes connecting elements 25 providing a mechanical connection to an articulation 24 (corresponding to the rotating arm according to FIGS. 1 to 5) and for example a further articulation 24 (corresponding to the hinge between the rotating arm and the integrated pivoting arm according to FIGS. 1 to 5), the connecting element 26 (corresponding to the connecting interface) or the fastening element 27 (corresponding to the displaceable base according to FIGS. 1 to 5). A connecting element 25 can be a mounting plate, for instance, by which the one articulation 24 and for instance the further articulation 24, the connecting element 26 or the fastening element 27 is non-positively fixed.

The individual articulations (hinges/axis of rotation) 24 as well as the connecting element 26 and the fastening element 27 are connected via mechanical connecting elements 25 (pivoting arms/rotating arm) so that by actuating the articulations 24 the connecting element 26 can be positioned relative to the fastening element 27 at least along the three spatial axes at right angles with each other.

Basically the positioning device 21 according to aspects of the invention offers the possibility of equipping selected or all actuator 22—connecting element 23—articulation 24—units with sensors which fulfill safety functions for the positioning device 21.

In an advantageous configuration of one (or more) selected actuator 22 said actuator 22 includes a sensor element (as is basically shown in FIG. 18b) capable of measuring the force to be transmitted. In another advantageous configuration of the actuator 22, said actuator 22 includes a device (cf. FIG. 17c) capable of measuring the energy applied by the actuator 22 to generate force. In another advantageous configuration of the actuator 22, said actuator 22 includes a device (cf. FIG. 17c) capable of mechanically limiting the force to be transmitted. In another advantageous configuration of the actuator 22, said actuator 22 includes a device (limit stops not represented in detail) capable of mechanically limiting the working range of the actuator 22. In another advantageous configuration of the actuator 22, said actuator 22 includes a device not shown in detail capable of exerting a constant operating force on the operating element of said actuator 22.

In an advantageous configuration of the transmission element 23, said transmission element 23 includes a device (cf. FIGS. 18a and 18b) capable of mechanically limiting the force to be transmitted. In a further advantageous configuration of the transmission element 23, said transmission element 23 includes a device (limit stops not represented in detail) capable of mechanically limiting the working range of the transmission element 23. In a further advantageous configuration of the transmission element 23, said transmission element 23 includes a sensor element capable of measuring the force to be transmitted. In a further advantageous configuration of the transmission element 23, said transmission element 23 includes a device capable of exerting a constant operating force on said transmission element 23.

In an advantageous configuration of the articulation 24, said articulation 24 includes a device (cf. FIGS. 17a and 18c) capable of mechanically limiting the operating force of said articulation 24. In another advantageous configuration of the articulation 24, said articulation 24 includes a device (limit stops not represented in detail) capable of mechanically limiting the operating range of said articulation 24. In another advantageous configuration of the articulation 24, said articulation 24 includes a sensor element (cf. FIG. 17a) capable of measuring the operating force of the articulation 24. In another advantageous configuration of the articulation 24, said articulation 24 includes a device capable of exerting a constant operating force on said articulation 24.

In an advantageous configuration of the positioning device 21, said positioning device 21 includes one or more housings 19 movably supported relative to each other.

In an advantageous configuration of each housing 19, said housing 19 includes at least one sensor element 10 (cf. especially FIG. 15a to 15c). Each sensor element 10 is used for detecting forces acting on the housing 19 that have occurred by collision.

In an advantageous configuration of the sensor element 10, said sensor element 10 is a deformation sensor and is connected to the housing 19 such that it can record deformations in a delimited area of the housing 19 and therefrom the force introduced to the housing can be concluded.

In an advantageous configuration of the sensor element 10, said sensor element 10 is a force sensor and is connected to the (each) housing 19 so that it can record, as connecting element between two elements of the housing 19, a force acting on either of the elements which is introduced from outside.

In an advantageous configuration of the sensor element 10, said sensor element 10 is a mechanical switch and is connected to the (each) housing 19 so that it acts as connecting element between two elements of the housing 19 and guides a force introduced from outside to either of the elements for operating the sensor element 10.

In an advantageous configuration of the sensor element 10, said sensor element 10 is a force-sensitive element attached to the outside of the (each) housing 19 so that contact forces acting on the sensor element 10 are recorded.

In an advantageous configuration of the housing 19, said housing 19 includes an operating element 11.

In an advantageous configuration of the operating element 11, said operating element 11 includes at least one handle which permits operation of the positioning device 21.

In another advantageous configuration of the operating element 11, said operating element 11 includes at least one touch-sensitive switch, for instance for manual operation of an appropriately encased actuator 22.

In another advantageous configuration of the operating element 11, said operating element 11 includes at least one optical display element.

Technical Measures to Ensure' Safety of the Patients

Risks for patients by the robot-guided orientation of the magnetic field generator of compact design 1 are resulting, inter alia, from the motions of the positioning device 21 for orientating the magnetic field generator of compact design 1 which may entail collisions with or action of force upon the patient's body and thus impacts on the patient's body endangering the patient. The following number of technical measures according to aspects of the invention is especially suited to ensure safety of the patients to this effect:

a monitoring device 31 for monitoring the position and forces occurring, as it is shown in total in the FIGS. 17a-17c and 18a-18c, the positioning device 21 capable of detecting, displaying or preventing operating states of the positioning device 21, especially operating states of the positioning device 21 endangering the patient, preferably in combination with a control system 28, a position limiting device capable of (mechanically or virtually) limiting the operating range of the positioning device 21, and a force limiting device capable of limiting forces occurring at the positioning device 21.

A collision of the positioning device 21 with or action of force of the positioning device 21 upon the patient's body can be detected by means of the monitoring device 31. Such monitoring device 31 can be, for instance, a sensor element capable of measuring the forces occurring in the positioning device 21 or acting upon the positioning device 21.

An advantageous configuration of the monitoring device 31 is a sensor element 10, for example in one of said advantageous configurations. Thus the monitoring device 10 is capable of measuring the forces acting upon the housing 19 of the positioning device 21 and in this way of admitting conclusions about the forces acting on a patient's body in the case of collision.

In another advantageous configuration of the monitoring device 31, said monitoring device 31 is a sensor element capable of measuring the forces acting in the articulation 24.

In another advantageous configuration of the monitoring device 31, said monitoring device 31 is a sensor element capable of measuring the position of the articulation 24.

In another advantageous configuration of the monitoring device 31, said monitoring device 31 is a sensor element capable of measuring the forces acting in the transmission element 23.

In another advantageous configuration of the monitoring device 31, said monitoring device 31 is a sensor element capable of measuring the position of the transmission element 23.

In another advantageous configuration of the monitoring device 31, said monitoring device 31 is a sensor element capable of measuring the forces occurring in the actuator 22.

In another advantageous configuration of the monitoring device 31, said monitoring device 31 is a device capable of measuring the energy applied by the actuator 22 for generating force.

In another advantageous configuration of the monitoring device 31, said monitoring device 31 is a sensor element capable of measuring the position of the actuator 22.

In an advantageous configuration of the monitoring device 31, said monitoring device 31 is operated in combination with a control system 28. The control system 28 is connected via a transmission element 29 for data to the monitoring device 31 so that data about the condition of the parameter to be monitored by the monitoring device 31 are transmitted from the monitoring device 31 to the control system 28. Moreover, the control system 28 is connected directly or indirectly to the actuator 22 via a transmission element 30 for data so that the control system 28 is capable of influencing the operating state of the actuator 22. The feedback of the parameters to be monitored by the monitoring device 31 via a control system 28 to the actuator 22 forms a closed control loop. This advantageous configuration enables the positioning device 21 not only to detect but optionally also to prevent actions of force upon the patient's body endangering the patient.

The control system 28 can be selectively provided inside or outside the housing 19 of the positioning device 21.

In case that the risk of impacts endangering the patient by a collision of the positioning device 21 with or without an action of force of the positioning device 21 on the patient's body can be associated with areas of the operating range of the positioning device 21, by means of a position limiting device the risk of a collision of the positioning device 21 with or an action of force of the positioning device 21 upon the patient's body can be excluded in particular areas of the operating range of the positioning device 21. Such position limiting device can be, for instance, a mechanical stop capable of mechanically limiting the operating range of an articulation 24 or it is a freely programmable virtual stop upon reaching a defined position in space.

Upon collision of the positioning device 21 with or an action of force of the positioning device 21 upon the patient's body the force acting upon the patient's body can be limited by means of a force limiting device 32. Such force limiting device 32 can be a safety-friction clutch of a known design which can transmit a torque from a first axis to a second axis only up to a defined maximum value. The force limiting device 32 preferably is configured such that the force limitation is obtained by a structural design of the force limiting device 32.

In an advantageous configuration of the force limiting device 32, said force limiting device 32 is a safety-friction clutch, however, which is connected to the transmission element 23 such that a force introduced by the actuator 22 to a first element 33 of the transmission element 23 is introduced to a second element 34 of the transmission element 23 only up to a defined maximum force.

In a further advantageous configuration of the force limiting device 32 the transmission element 23 comprises a force transmission mechanism with the help of a toothed belt or V-belt, wherein the force limiting device 32 is a toothed belt pulley or V-belt pulley including a device which is capable of transmitting the force applied to the toothed belt pulley or V-belt pulley to a consumer only up to a defined maximum force, the consumer for instance being a shaft, a toothed belt or V-belt.

In a further advantageous configuration of the force limiting device 32, said force limiting device 32 is an integral part of the actuator 22 which is capable of limiting the force generated by the actuator 22 to a defined maximum value. It is possible, for instance, to integrate the force limiting device 32 in the actuator by using a step motor as actuator which, inherent in design, falls out of synchronism upon exceeding a predetermined force (torque), and thus the driving force becomes quasi zero.

In a further advantageous configuration of the force limiting device 32, said force limiting device 32 is an integral part of the articulation 24 which is capable of limiting the force applied by the articulation 24 to the mechanical connecting element 25 to a defined maximum value.

An operating device 35 (corresponding to the afore-mentioned actuator 22—connecting element 23—articulation 24—unit) includes at least one actuator 22, at least one transmission element 23, at least one articulation 24 as well as at least one mechanical connecting element 25 (cf. e.g. FIG. 17a). Such operating device 35 can be considered to be a functional unit comprising at least these components.

In an advantageous further development of the operating device 35 the mechanical connecting element 25 consists of a first connecting element 41 and a second connecting element 42, both the first connecting element 41 and the second connecting element 42 being coupled to the articulation 24 such that between the first connecting element 41 and the second connecting element 42 a relative (e.g. hinge-type) movement substantially predetermined by the articulation 24 is possible.

Figure 19A:
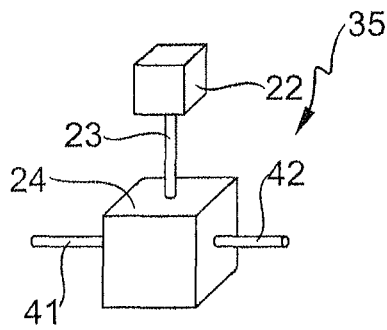
Figure 19B:
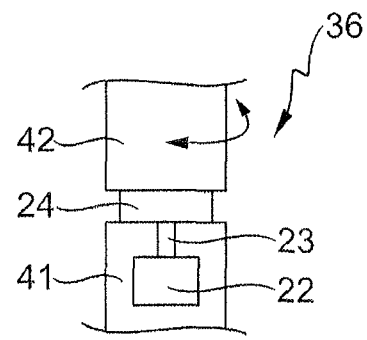
Figure 19C:
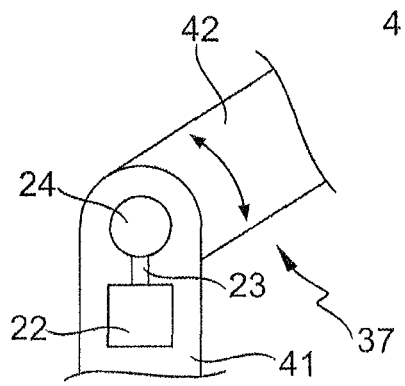
Figure 19D:
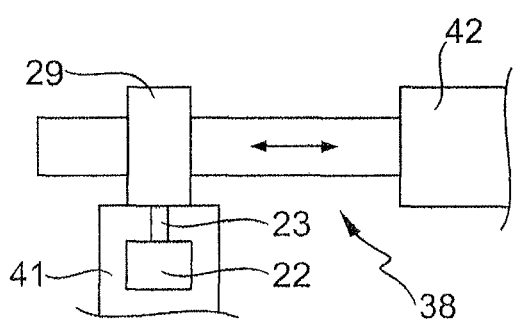
Figure 19E:
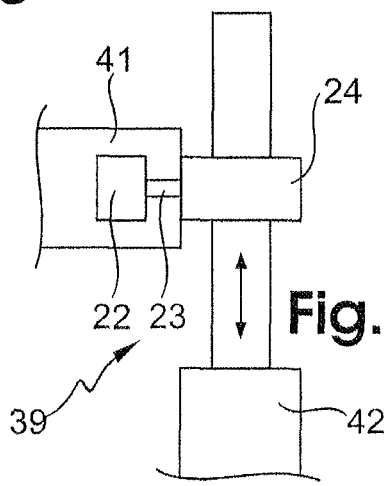
Figure 19F:
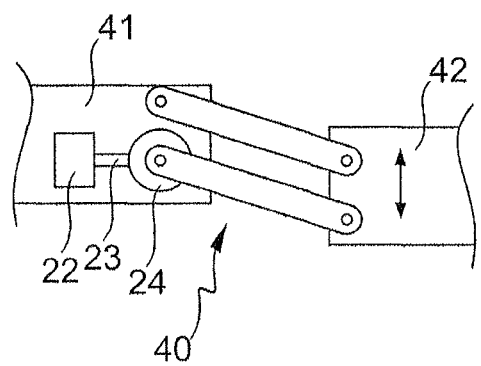

Different characteristics of the operating device 35 are known, wherein five different characteristics of the operating device 35 thereof are exemplified hereinafter:

- an operating device 36 for rotation about a vertical axis (cf. FIG. 19b),
- an operating device 37 for rotation/pivoting about a horizontal axis (cf. FIG. 19c),
- an operating device 38 for translation along a horizontal axis (cf. FIG. 19d),
- an operating device 39 for translation along a vertical axis (cf. FIG. 19e) and
- an operating device 40 for parallel shift mainly in the vertical direction (cf. FIG. 19f).

The operating device 36 for rotation about a vertical axis is shown by way of example in FIG. 19b. In this case basically a rotational drive is concerned, for instance an electric motor or a transmission for transforming a translational motion into a rotational motion such as a combination of toothed rack and gearwheel. This device is used, inter alia, as actuator between the base and the rotating arm of the positioning device according to FIGS. 1 through 5.

The operating device 37 for rotation/pivoting about a horizontal axis is exemplified in FIG. 19c and can comprise either a rotational drive according to the foregoing definition or a translational drive such as a piston-cylinder unit which acts upon a central portion of the coupled connecting elements which are connected to each other via a hinge.

The operating device 38 for translation along a horizontal axis is exemplified in FIG. 19d and can relate to a generally known telescopic mechanism, a toothed rack or a piston-cylinder unit.

The operating device 39 for translation along a vertical axis is exemplified in FIG. 19e and has a structural design comparable to FIG. 19d. However, it is advantageous in this context that the operating device 39 is force-balanced for example by connecting a spring in parallel so that substantially only inertia moments (and possibly frictional forces) act upon the drive for operating e.g. the toothed rack/telescopic rod.

The operating device 40 for parallel shift mainly in vertical direction is exemplified in FIG. 19f. In this case it is formed by a parallel hinge consisting of at least two parallel levers each being hinge-like coupled at its end side to a connecting element. At least one of the levers is driven according to the principle of the operating device 37.

The functional principle of the afore-mentioned operating devices can be summarized as follows:

In the operating devices 36 and 38 the operation by the actuator is independent of the force by the dead weight. In the operating devices 37, 39 and 40 the operation by force is influenced by the dead weight. Therefore, in addition to the operating force the actuator 22 must generate a force which is opposed to the force by the dead weight. This force can be dependent on the position of the operating device (as in the case of the operating devices 37 and 40) or can be independent, i.e. constant (as in the case of the operating device 39).

The necessity to maintain a force exceeding the actual operating force by the actuator 22 entails the necessity to appropriately provide this when designing the actuator 22 as represented in the table according to FIG. 6. Consequently, the actuator 22 is required to be able to generate a higher force than it is required for the actual operation. In the case of malfunction of the monitoring device 31 and the force limiting device 32 or in the case of incorrect operation, for example, there is the risk that the force maintained by the actuator 22 acts upon the patient's body and leads to impacts on the patient's body endangering the patient.

The solution according to aspects of the invention is the implementation of force compensation, preferably by a structural device (biasing spring/balancing weights via lever mechanisms). In this way the design of the actuator 22 can be such that the actuator 22 cannot generate a force that exceeds the force required to operate the operating device 35. The force required for operating the operating device 35 preferably is not greater than the force allowed to maximally act upon the patient's body without generating an impact on the patient's body endangering the patient. This measure quasi excludes the risk that the force acting upon the patient's body results in impacts endangering the patient even in the case of malfunction of the monitoring device 31 or the force limiting device 32 according to the foregoing description or in the case of incorrect operation of the magnetic guiding device (robotics) comprising the positioning device and the end effector.

LIST OF REFERENCE NUMERALS

Degree of freedom a: translational motion of the magnetic field generator of compact design along the space axis x
Degree of freedom b: translational motion of the magnetic field generator of compact design along the space axis y
Degree of freedom c: translational motion of the magnetic field generator of compact design along the space axis z
Degree of freedom d: rotational motion of the magnetic field generator of compact design about the internal axis A in 0-position (or about the Y-axis of the space coordinate system independently of the position of the magnetic field generator)
Degree of freedom e: rotational motion of the magnetic field generator of compact design about the internal axis B
  1 magnetic field generator of compact design
  2 space axis x of the magnetic field generator of compact design
  3 space axis y of the magnetic field generator of compact design
  4 space axis z of the magnetic field generator of compact design
  5 space axis a of the magnetic field generator of compact design
  6 space axis b of the magnetic field generator of compact design
  7 polarization axis of the magnetic field generator of compact design
  8 actuator for actuating a rotational degree of freedom
  9 transmission element for actuating a rotational degree of freedom
  10 sensor element
  11 operating element
  12 housing of the magnetic end effector
  13 magnetic end effector
  14 connecting element for the transmission of forces
  15 connecting element for the transmission of energy
  16 connecting element for the transmission of data
  17 sensor element
  18 sensor element
  19 housing of the positioning device
  20 operating element
  21 positioning device
  22 actuator
  23 transmission element
  24 articulation
  25 mechanical connecting element
  26 connecting element for the transmission of forces
  27 fastening element
  28 control system
  29 transmission element for data
  30 transmission element for data
  31 monitoring device
  32 force limiting device
  33 first element of the transmission device
  34 second element of the transmission device
  35 operating device
  36 operating device for rotation about a vertical axis
  37 operating device for rotation about a horizontal axis
  38 operating device for translation along a horizontal axis
  39 operating device for translation along a vertical axis
  40 operating device for parallel shift mainly in vertical direction
  41 first connecting element
  42 second connecting element
  100 guiding device
  102 positioning device
  104 effector (housing)
  106 connecting interface
  108/110 pivoting arms
  112/116 hinged joint
  114/122/124/128 actuator
  118 rotating arm
  120 horizontal hinge
  126 base
  132 extension/telescopic rod
  130/134 actuator
  136 vertical hinge
  138 push rod
  140 lever arm
  142 weight
  144 push-pull rod
  146 lever rod
  148 tie rod
  150 (balancing) weight

The invention claimed is:

1. An extracorporeal guiding device for an intracorporeal magnetic object, the extracorporeal guiding device comprising:
  a motor-driven positioning device;
  a distal connecting interface connected to the positioning device; and
  an end effector connected to the distal connecting interface, the end effector comprising:
    a housing connected to the distal connecting interface by a coupling;
    a magnetic field generator inside the housing; and
    at least one actuator connected to the magnetic field generator inside the housing,
  the motor-driven positioning device providing a maximum of three degrees of freedom for moving the distal connecting interface in translation along a maximum of three axes in an extracorporeal space coordinate system;
  the at least one actuator inside the housing providing a maximum of two degrees of freedom for rotating the magnetic field generator about a maximum of two axes of rotation inside the housing in the space coordinate system; and
  the coupling supporting and maintaining the housing in a fixed orientation relative to the positioning device during translation of the distal connecting interface and during rotation of the magnetic field generator inside the housing, such that the orientation of the housing remains constant and independent of any translation of the distal connecting interface and any rotation of the magnetic field generator during extracorporeal guidance of the intracorporeal magnetic object, wherein the three degrees of freedom of the positioning device exclusively allow a translational motion of the distal connecting interface in an X-, Y- and Z-direction of the space coordinate system in which a Y-axis is orientated substantially along a gravity direction and a Z-axis is orientated along a longitudinal and thus polarization axis of the magnetic field generator, whereas the two degrees of freedom of the at least one actuator exclusively allow a respective rotational motion of the magnetic field generator about the Y- and X-axis of the space coordinate system so as to cause yawing and pitching of the magnetic field generator with respect to the space coordinate system.

2. The extracorporeal guiding device according to claim 1, wherein only one rotational degree of freedom of the at least one actuator is encased for pitching of the magnetic field generator and for rotating of the magnetic field generator about the X-axis, the housing or at least part of the housing is pivot-mounted for yawing of the magnetic field generator supported therein for rotating about the Y-axis at the connecting interface.

3. The extracorporeal guiding device according to claim 1, wherein both degrees of freedom of the at least one actuator are encased for pitching and yawing, whereas the housing is maintained in its spatial orientation independently of a motion of the positioning device.

4. An extracorporeal guiding device for an intracorporeal magnetic object, the extracorporeal guiding device comprising:
 a motor-driven positioning device;
 a distal connecting interface connected to the positioning device; and
 an end effector connected to the distal connecting interface, the end effector comprising:
  a housing connected to the distal connecting interface by a coupling;
  a magnetic field generator inside the housing; and
  at least one actuator connected to the magnetic field generator inside the housing,
 the motor-driven positioning device providing a maximum of three degrees of freedom for moving the distal connecting interface in translation along a maximum of three axes in an extracorporeal space coordinate system;
 the at least one actuator inside the housing providing a maximum of two degrees of freedom for rotating the magnetic field generator about a maximum of two axes of rotation inside the housing in the space coordinate system; and
 the coupling supporting and maintaining the housing in a fixed orientation relative to the positioning device during translation of the distal connecting interface and during rotation of the magnetic field generator inside the housing, such that the orientation of the housing remains constant and independent of any translation of the distal connecting interface and any rotation of the magnetic field generator during extracorporeal guidance of the intracorporeal magnetic object,
 wherein the three degrees of freedom of the positioning device allow a translational motion of the distal connecting interface in an X-, Y- and Z-direction of the space coordinate system in which the Y-axis is orientated substantially along a gravity direction, whereas each of the two degrees of freedom of the end effector allows a rotational motion of the magnetic field generator so as to cause pivoting substantially about a vertical axis and pitching of a polarization axis of the magnetic field generator with respect to the space coordinate system.

5. The extracorporeal guiding device according to claim 4, wherein the housing comprises either substantially closed housing walls and/or an open grid/frame structure.

6. The extracorporeal guiding device according to claim 4, wherein the positioning device includes a number of motor-driven extensions or arms, wherein selected extensions or arms thereof are weight-balanced with respect to corresponding motor drives, for which purpose such balancing system is provided which performs or causes a dynamic adaptation of a weight balancing to a weight load currently acting upon a respective motor drive.

7. The extracorporeal guiding device according to claim 4, wherein the positioning device includes a number of motor-driven extensions or arms, wherein selected extensions or arms thereof are supported with respect to corresponding motor drives, so that the motor drives have to absorb or overcome either no or only a small static weight load, for which purpose a predetermined direction of movement of the extensions points substantially normal to gravity.

8. The extracorporeal guiding device according to claim 4, wherein a respective motor drive for selected degrees of freedom either is or becomes limited as to a driving force in such manner that the driving force adapted to be maximally output is either equal to or greater than an operating load force to be expected, but equal to or smaller than a predetermined maximum force in the case of which an injury to a patient or an operator in an event of collision is largely excluded.

9. The extracorporeal guiding device according to claim 4, wherein a respective motor drive for selected degrees of freedom is limited as to the driving force by a connected safety-friction clutch or safety clutch, an upstream electric power or hydraulic/pneumatic pressure limiter or by use of a step motor.

10. The extracorporeal guiding device according to claim 4, wherein a respective motor drive includes an electric motor, a piezo element, a hydraulic/pneumatic piston-cylinder unit or a magnetic drive.

11. The extracorporeal guiding device according to claim 4, wherein a monitoring means to which a number of sensors is connected for monitoring an operating state of the guiding device and for correcting the operating state and/or turning off the guiding device when a predetermined risk of accident is detected.

12. The extracorporeal guiding device according to claim 11, wherein the sensors are selected from a group of sensors consisting of:
 a force sensor for detecting a drive load,
 a touch or force sensor for detecting a contact force between the magnetic end effector or a selected extension of the positioning device and an operator or a patient,
 a deformation detection sensor for detecting an indentation at the end effector housing,
 an optical sensor for optically detecting obstacles, and
 a distance sensor for detecting a distance from obstacles.

13. The extracorporeal guiding device according to claim 4, wherein motion limiting means are in the form of programmed/programmable and/or mechanical limit stops/limit switches mounted to the positioning device and/or the at least one actuator such that a selection of the maximum of three degrees of freedom of the positioning device and/or the maximum of two degrees of freedom of the at least one actuator is mechanically restricted to a predetermined range of motion.

14. The extracorporeal guiding device according to claim 4, wherein, when only one or both degrees of freedom of the at least one actuator are encased, the housing is connected to the distal connecting interface of the positioning device such that it is orientated substantially in the gravity direction with or without an inherent motor drive as well as independently of a current motion of the positioning device and/or of the magnetic field generator in such manner that a provided contact face at the housing always maintains the same orientation with respect to the gravity direction.

15. The extracorporeal guiding device according to claim 4, wherein the magnetic field generator is a permanent magnet.

* * * * *